(12) United States Patent
Ishii et al.

(10) Patent No.: US 7,183,423 B1
(45) Date of Patent: Feb. 27, 2007

(54) PROCESS FOR THE PREPARATION OF ORGANIC COMPOUNDS WITH IMIDE CATALYSTS

(75) Inventors: Yasutaka Ishii, Takatsuki (JP); Takahiro Iwahama, Suita (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 478 days.

(21) Appl. No.: 09/622,001

(22) PCT Filed: Dec. 9, 1999

(86) PCT No.: PCT/JP99/06891

§ 371 (c)(1), (2), (4) Date: Sep. 22, 2000

(87) PCT Pub. No.: WO00/35835

PCT Pub. Date: Jun. 22, 2000

(30) Foreign Application Priority Data

| Dec. 11, 1998 | (JP) | ................................. | 10-353621 |
| Dec. 11, 1998 | (JP) | ................................. | 10-353622 |
| Mar. 11, 1999 | (JP) | ................................. | 11-065651 |
| May 17, 1999 | (JP) | ................................. | 11-136340 |

(51) Int. Cl.
*C07D 305/12* (2006.01)
*C07D 307/32* (2006.01)
*C07D 307/34* (2006.01)
*C07D 307/56* (2006.01)

(52) U.S. Cl. ....................... 549/313; 549/319
(58) Field of Classification Search ............... 549/313, 549/319
See application file for complete search history.

(56) References Cited

FOREIGN PATENT DOCUMENTS

| JP | A63135378 | 6/1988 |
| JP | A990637 | 4/1997 |
| JP | A9110851 | 4/1997 |
| JP | A10212283 | 8/1998 |
| JP | A19840337 | 9/1998 |
| JP | A10307396 | 11/1998 |
| WO | WO 99/50204 | 10/1999 |

OTHER PUBLICATIONS

Brenna et al, Tetrahedron, vol. 53, No. 30, pp. 10555-10564, (1997).
Fronza et al, The Journal of Organic Chemistry, vol. 59, No. 12, pp. 3487-3489, (Jun. 17, 1994).
Fogliato et al, The Journal of Organic Chemistry, vol. 60, No. 17, pp. 5693-5695, (Aug. 25, 1995).
Grochowski et al, International Journal of Methods In Synthetic Organic Chemistry, No. 10, pp. 718-720, (Oct. 1977).
Roudier et al, Tetrahedron Letters, vol. 25, No. 39, pp. 4375-4378, (1984).
Fronza et al, Biotechnology Letters, vol. 16, No. 10, pp. 1047-1052, (Oct. 1994).
Munoz et al, Journal of Chemical Research, Issue 2, pp. 68-69, (Feb. 1993).
Fronza et al, Tetrahedron Letters, vol. 33, No. 38, pp. 5625-5628, (1992).
Seebach et al, Helvetica Chimica Acta, vol. 63, Fasc. 1, (1980).

*Primary Examiner*—Taofiq Solola
(74) *Attorney, Agent, or Firm*—Birch, Stewart, Kolasch & Birch, LLP

(57) ABSTRACT

(A) A compound capable of forming a stable radical and selected from (A1) oxygen-atom-containing compounds each having a carbon-hydrogen bond at the adjacent position to an oxygen atom, (A2) carbonyl-group-containing compounds, and (A3) compounds each having a hydrocarbon group with a methine carbon atom is allowed to react with (B) a radical scavenging compound selected from, for example, (B1) unsaturated compounds, and (B2) compounds each having a hydrocarbon group with a methine carbon atom, in the presence of molecular oxygen by catalysis of, for example, an imide compound shown by the following formula (1):

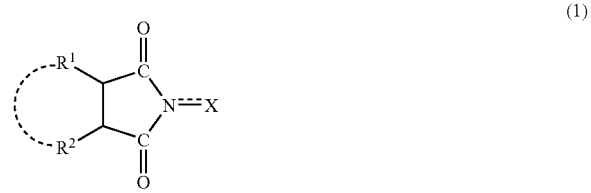

(1)

wherein each of $R^1$ and $R^2$ is a hydrogen atom or the like, where $R^1$ and $R^2$ may be combined to form a double bond, or an aromatic or non-aromatic ring; X is an oxygen atom or a hydroxyl group, to yield a product of an addition or substitution reaction of the compound (A) and the compound (B) or its oxidized product.

The process can efficiently produce a variety of organic compounds by an addition or substitution reaction using molecular oxygen under mild conditions.

5 Claims, No Drawings

US 7,183,423 B1

PROCESS FOR THE PREPARATION OF ORGANIC COMPOUNDS WITH IMIDE CATALYSTS

This application is the national phase under 35 U.S.C. § 371 of PCT International Application No. PCT/JP99/06891 which has an International filing date of Dec. 9, 1999, which designated the United States of America.

TECHNICAL FIELD

This invention relates to a process for producing an organic compound using an imide compound catalyst. Specifically, the invention relates to a process of allowing two compounds to react with each other in the presence of a specific imide compound and a radical generator with respect to the imide compound to yield a product of an addition or substitution reaction or an oxidized product thereof by a radical mechanism. The invention also relates to a process for producing a hydroxy-γ-butyrolactone derivative which is useful as, for example, a material for pharmaceuticals, agricultural chemicals, and other fine chemicals, photosensitive resins and other functional polymers. In addition and advantageously, the invention relates to a novel α-hydroxy-γ-butyrolactone derivative, to a novel α-(meth) acryloyloxy-γ-butyrolactone derivative, to a polymer including the compound just mentioned above as a monomeric unit, to a photosensitive resinous composition containing the polymer, and to a novel γ-butyrolactone derivative having a bridged cyclic hydrocarbon group.

BACKGROUND ART

Some useful organic compounds are known to be produced by adding a variety of compounds to an unsaturated compound having, for example, a carbon—carbon double bond or a heteroatom-containing compound. For example, when an active methylene compound such as a malonic diester is allowed to react with an olefin having an electron attracting group such as acrylonitrile in the presence of a base, a carbon—carbon bond is formed by a nucleophilic addition reaction to yield an adduct (Michael addition reaction). When two carbonyl compounds are treated in the presence of an acid or a base, one carbonyl compound is nucleophilically added to the other carbonyl compound and a carbon—carbon bond is formed to yield an aldol condensate.

However, a reaction is generally performed in the presence of an acid or a base according to these processes, and these processes cannot be applied to compounds having substituents that are unstable to acids or bases. According to these processes, for example, a hydroxymethyl group, an alkoxymethyl group, an acyl group, or a tertiary carbon atom cannot be directly bonded to a carbon atom of an unsaturated bond of an unsaturated compound or to a methine carbon atom of a bridged cyclic compound.

Addition reactions to carbon—carbon double bonds and coupling reactions to form carbon—carbon bonds through radical mechanism are also known. However, there is significantly no process for efficiently obtaining addition or substitution reaction products or oxidized products thereof, for example, with molecular oxygen under mild conditions.

Separately, some processes are known as production processes of hydroxy-γ-butyrolactone derivatives. For example, European Unexamined Patent Application Publication No. 2103686 discloses a process for synthetically obtaining pantolactone by allowing glyoxylic acid to react with isobutylene. Japanese Unexamined Patent Application Publication No. 61-282373 discloses a process also for synthetically obtaining pantolactone, by allowing glyoxylic hydrate to react with t-butyl alcohol. Tetrahedron, 933 (1979) discloses a process for synthetically obtaining pantolactone. This process includes the steps of hydrolyzing 4-hydroxy-2-methyl-5,5,5-trichloro-1-pentene to yield 2-hydroxy-4-methyl-4-pentenoic acid, and cyclizing this compound in the presence of hydrochloric acid. In addition, The Chemical Society of Japan, Spring Annual Meeting, Lecture Proceedings II, pp. 1015 (1998) reports that light irradiation to a mixture solution containing an α-acetoxy-α, β-unsaturated carboxylic ester and 2-propanol yields a corresponding α-acetoxy-γ,γ-dimethyl-γ-butyrolactone derivative. However, each of these processes employs a material that is not easily available, or requires special conditions for the reaction.

Of the butyrolactone derivatives, the following derivatives are not known: (1) spiro-type γ-butyrolactone derivatives each having a hydroxyl group at the α-position and a non-aromatic carbon ring bonded to the γ-position, (2) γ-butyrolactone derivatives each having a hydroxyl group at the α-position, a haloalkyl group, a substituted oxycarbonyl group, a cyano group, or an aryl group at the β-position, and a hydrogen atom, a hydrocarbon group or a heterocyclic group bonded to the γ-position, (3) γ-butyrolactone derivatives each having a hydroxyl group at the α-position, and a hydrogen atom and a group selected from hydrocarbon groups and heterocyclic groups bonded to the γ-position, and (4) α-hydroxy-γ-butyrolactone derivatives each having a bridged cyclic hydrocarbon group bonded to the γ-position, and (meth)acryloyl derivatives thereof. In addition, substantially no process can easily and efficiently produce γ-butyrolactone derivatives each having a hydroxyl group at the β-position.

Separately, a lithography technique is used for the formation of fine patterns of semiconductor integrated circuits. The lithography technique includes the steps of covering the substrate having a thin film formed thereon (work) with a resist, subjecting the work to selective exposure to yield a latent image of a target pattern, subjecting the work to developing to form a patterned resist, dry-etching the work using the pattern as a mask, and then removing the resist to yield the target pattern. In this lithography technique, g-ray, 1-ray, and other ultraviolet rays are used as light sources. However, with an increasing fineness of patterns, far ultraviolet rays, vacuum ultraviolet rays, excimer laser beams, electron beams, x-rays and other rays having a shorter wavelength are employed as the light sources.

To form fine patterns using such a short-wavelength light source (e.g., ArF excimer laser), the resist used must have a satisfactory transparency at the wavelength of the light source, have a good adhesion to the substrate, be resistance to dry etching, and be satisfactorily soluble in a developer in development. As such resist materials, polymers of polymerizable monomers each having a bridged ring or a lactone ring have receive attention in recent years.

For example, Japanese Unexamined Patent Application Publication No. 9-73173 proposes a resist material as a photoresist suitable for a short-wavelength light source. This resist material includes a polymer and an acid generator, and the polymer comprises a structural unit which is protected by adamantane or another alicyclic hydrocarbon group and is to be eliminated by action of an acid to make the polymer soluble in alkalis. The resist material includes no aromatic ring, is thus transparent to the ArF excimer laser light or the like, and is satisfactorily resistant to dry etching. However, the resist material may not be rapidly dissolved in a developer, because the protective moiety is not sufficiently eliminated by an acid generated through light irradiation. Accordingly, the resist material is still insufficient in definition (photosensitivity, sensitivity), and is still insufficient in adhesion to a substrate.

DISCLOSURE OF INVENTION

Accordingly, an object of the invention is to provide a process for efficiently producing an organic compound by an addition or substitution reaction under mild conditions.

Another object of the invention is to provide a process for producing an organic compound, which can bond, for example, a hydroxymethyl group, an alkoxymethyl group, an acyl group, or a tertiary carbon atom directly to, for example, a carbon atom of an unsaturated bond of an unsaturated compound or to a methine carbon atom of a bridged cyclic compound.

A further object of the invention is to provide a process for obtaining a corresponding 1,3-dihydroxy compound in a good yield from an alcohol, an unsaturated compound, and oxygen.

Yet another object of the invention is to provide a process for producing an α-hydroxy-γ-butyrolactone derivative from easily available materials under mild conditions.

Still another object of the invention is to provide a spiro-type α-hydroxy-γ-butyrolactone derivative having a non-aromatic carbon ring bonded to the γ-position.

Another object of the invention is to provide a process for easily and efficiently producing a β-hydroxy-γ-butyrolactone derivative.

Yet another object of the invention is to provide a sensitive resinous composition that is rapidly dissolved in a developer by actin of an acid generated through light irradiation and can stably and precisely form fine patterns, and to provide an acid-sensitive polymer and material compounds thereof which are useful for obtaining the sensitive resinous composition.

A further object of the invention is to provide a sensitive resinous composition that can form a resist film having a satisfactory adhesion to a substrate, and to provide an acid-sensitive polymer and its material compound which are useful for obtaining the sensitive resinous composition.

Still another object of the invention is to provide a novel α-hydroxy-γ-butyrolactone derivative having a bridged cyclic hydrocarbon group bonded to the γ-position and its (meth)acryloyl derivative.

Another object of the invention is to provide a novel γ-butyrolactone derivative, which is useful as a monomeric material of an acid-sensitive polymer constituting a photoresist resinous composition.

Yet another object of the invention is to provide a corresponding conjugated unsaturated compound from an alcohol, an unsaturated compound, and oxygen.

A further object of the invention is to provide a process for producing a corresponding β-hydroxyacetal compound from an acetal, an unsaturated compound, and oxygen in a good yield.

Still another object of the invention is to provide a process for producing a corresponding hydroxy compound from a compound having a methine carbon atom, an unsaturated compound, and oxygen in a good yield.

Another object of the invention is to provide a process for producing a corresponding carbonyl compound from a compound having a methine carbon atom, an unsaturated compound, and oxygen in a good yield.

Yet another object of the invention is to provide a process for producing a compound having an electron attracting group from a compound having a methine carbon atom, an unsaturated compound, and oxygen in a good yield.

A further object of the invention is to provide a process for producing a corresponding coupling product from an alcohol, a compound having a methine carbon atom, and oxygen in a good yield.

Still another object of the invention is to provide a process for producing a corresponding coupling product from a compound having a methine carbon atom, and oxygen in a good yield.

After intensive investigations to achieve the above objects, the present inventors found that the use of an imide compound having a specific structure can yield a corresponding addition or substitution reaction product or an oxidized product thereof, under mild conditions, through a reaction of a compound which is capable of forming a stable radical with a radical scavenging compound in the presence of oxygen and/or a radical generator with respect to the imide compound.

The present inventors also found that a corresponding α-hydroxy-γ-butyrolactone derivative can be obtained under mild conditions by a reaction of an alcohol with an α,β-unsaturated carboxylic acid derivative in the presence of molecular oxygen by catalysis of the imide compound having a specific structure; that the α-hydroxy-γ-butyrolactone derivative can be easily and efficiently isomerized into a corresponding β-hydroxy-γ-butyrolactone derivative by dissolving the α-hydroxy-γ-butyrolactone derivative in a solvent; and that when a polymer including a (meth)acrylate derivative derived from the α-hydroxy-γ-butyrolactone derivative is used as a photoresist resin, a lactone ring moiety is rapidly eliminated from the polymer by action of an acid formed from a light-activatable acid generator through light irradiation, and the polymer and the eliminated moiety can be easily dissolved in a developer and can be removed. This photoresist resin can markedly improve the definition and developing efficiency and has a satisfactory adhesion to a substrate.

They also found that a novel α-hydroxy-γ-butyrolactone derivative having a bridged cyclic hydrocarbon group bonded to the γ-position can be obtained by allowing an alcohol having a bridged cyclic hydrocarbon group to react with an α,β-unsaturated carboxylic acid derivative in the presence of molecular oxygen by catalysis of the imide compound having a specific structure; and that a novel γ-butyrolactone derivative can be obtained by converting the α-hydroxy-γ-butyrolactone derivative into a (meth)acryloyl derivative, where the γ-butyrolactone derivative is useful as a monomeric material of an acid-sensitive polymer.

In addition and advantageously, the present inventors found that a corresponding conjugated unsaturated compound or compound having an electron attracting group can be obtained under mild conditions by allowing a specific alcohol or a compound having a methine carbon atom to react with a specific unsaturated compound in the presence of molecular oxygen by catalysis of the imide compound having a specific structure.

The present invention has been accomplished on the basis of these findings.

Specifically, the invention provides a process for producing an organic compound. The process includes the step of allowing (A) a compound capable of forming a stable radical and selected from (A1)oxygen-atom-containing compounds each having a carbon-hydrogen bond at the adjacent position to an oxygen atom, (A2) carbonyl-group-containing compounds, and (A3) compounds each having a hydrocarbon group with a methine carbon atom to react with (B) a radical scavenging compound selected from (B1) unsaturated compounds, (B2) compounds each having a hydrocarbon group with a methine carbon atom, and (B3) heteroatom-containing compounds, provided that if a 1,2-dicarbonyl compound or its hydroxy reductant is used as the compound (A), the compound (B) is a radical scavenging compound selected from the compounds (B1) and (B3), in the presence of a catalytic imide compound shown by the following formula (1):

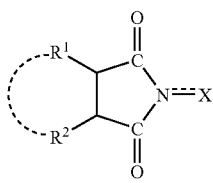
(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (1) may be further bonded to the $R^1$, $R^2$, or to the double bond or aromatic or non-aromatic ring formed together by $R^1$ and $R^2$, and in the presence of oxygen and/or a radical generator with respect to the imide compound, to yield a product of an addition or substitution reaction of the compound (A) and the compound (B) or an oxidized product thereof.

In the process for producing an organic acid, (A11) an alcohol shown by the following formula (2):

(2)

wherein each of $R^a$ and $R^b$ is, identical to or different from each other, a hydrogen atom or an organic group, where $R^a$ and $R^b$ may be combined to form a ring with the adjacent carbon atom, may be allowed to react with (B11) an active olefin shown by the following formula (3):

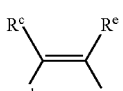
(3)

wherein each of $R^c$, $R^d$, and $R^e$ is, identical to or different from one another, a hydrogen atom or an organic group; and Y is an electron attracting group, where $R^c$, $R^d$, $R^e$, and Y may be combined to form a ring with the adjacent carbon atom or carbon—carbon bond, in the presence of molecular oxygen by catalysis of the imide compound of the formula (1), to yield a 1,3-dihydroxy compound shown by the following formula (4):

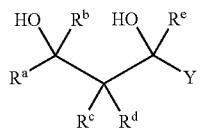
(4)

wherein $R^a$, $R^b$, $R^c$, $R^d$, $R^e$, and Y have the same meanings as defined above.

The invention provides, in another aspect, a process for producing an α-hydroxy-γ-butyrolactone derivative. This process includes the step of allowing (A11) the alcohol shown by the formula (2) to react with (B12) an α,β-unsaturated carboxylic acid derivative shown by the following formula (5):

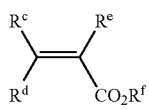
(5)

wherein each of $R^c$, $R^d$, $R^e$ and $R^f$ is, identical to or different from one another, a hydrogen atom or an organic group, where $R^c$, $R^d$ and $R^e$ may be combined to form a ring with the adjacent carbon atom or carbon—carbon bond, in the presence of molecular oxygen by catalysis of the imide compound of the (1) to yield an α-hydroxy-γ-butyrolactone derivative shown by the following formula (6):

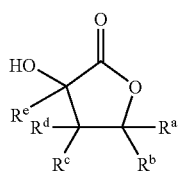
(6)

wherein $R^a$, $R^b$, $R^c$, $R^d$, and $R^e$ have the same meanings as defined above.

In a further aspect, the invention provides a process for producing a β-hydroxy-γ-butyrolactone derivative. The process includes the step of dissolving an α-hydroxy-γ-butyrolactone derivative shown by the following formula (6a):

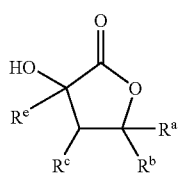
(6a)

wherein each of $R^a$ and $R^b$ is, identical to or different from each other, a hydrogen atom or an organic group, where $R^a$ and $R^b$ may be combined to form a ring with the adjacent carbon atom, and each of $R^e$ and $R^e$ is, identical to or different from each other, a hydrogen atom or an organic group, where $R^c$ and $R^e$ may be combined to form a ring with the adjacent carbon—carbon bond, in a solvent to yield a β-hydroxy-γ-butyrolactone derivative shown by the following formula (7):

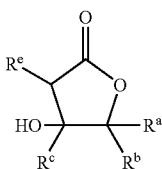

(7)

wherein $R^a$, $R^b$, $R^c$, and $R^e$ have the same meanings as defined above.

In another aspect, the invention provides an α-hydroxy-γ-butyrolactone derivative (hereinafter referred to as "α-hydroxy-γ-butyrolactone derivative 1") shown by the following formula (6b):

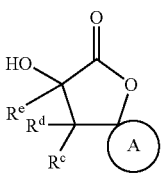

(6b)

wherein ring A is a non-aromatic carbon ring, each of $R^c$, $R^d$, and $R^e$ is, identical to or different from one another, a hydrogen atom or an organic group, where $R^c$, $R^d$, and $R^e$ may be combined to form a ring with the adjacent carbon atom or carbon—carbon bond.

In addition, the invention provides an α-hydroxy-γ-butyrolactone derivative (hereinafter referred to as "α-hydroxy-γ-butyrolactone derivative 2") shown by the following formula (6c):

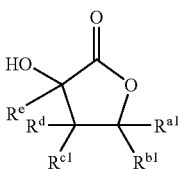

(6c)

wherein each of $R^{a1}$ and $R^{b1}$ is, identical to or different from each other, a hydrogen atom, a hydrocarbon group, or a heterocyclic group, where $R^{a1}$ and $R^{b1}$ may be combined to form a ring with the adjacent carbon atom; $R^{c1}$ is a haloalkyl group, a substituted oxycarbonyl group, a cyano group, or an aryl group; each of $R^d$ and $R^e$ is, identical to or different from each other, a hydrogen atom or an organic group, where $R^{c1}$, $R^d$, and $R^e$ may be combined to form a ring with the adjacent carbon atom or carbon—carbon bond.

The invention also provides another α-hydroxy-γ-butyrolactone derivative. This derivative (hereinafter referred to as "α-hydroxy-γ-butyrolactone derivative 3") is shown by the following formula (6d):

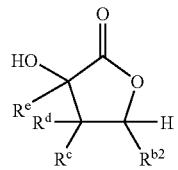

(6d)

wherein $R^{b2}$ is, identical to or different from each other, a hydrocarbon group or a heterocyclic group, and each of $R^c$, $R^d$, and $R^e$ is, identical to or different from one another, a hydrogen atom or an organic group, where $R^c$, $R^d$, and $R^e$ may be combined to form a ring with the adjacent carbon atom or carbon—carbon bond.

In yet another aspect, the invention provides an α-(meth)acryloyloxy-γ-butyrolactone derivative shown by the following formula (8):

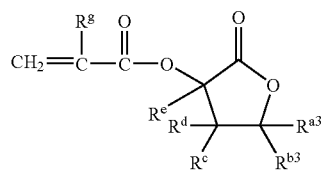

(8)

wherein each of $R^{a3}$ and $R^{b3}$ is, identical to or different from each other, a hydrogen atom, a hydrocarbon group, or a heterocyclic group, where $R^{a3}$ and $R^{b3}$ may be combined to form a ring with the adjacent carbon atom; each of $R^c$, $R^d$, and $R^e$ is, identical to or different from one another, a hydrogen atom or an organic group, where $R^c$, $R^d$, and $R^e$ may be combined to form a ring with the adjacent carbon atom or carbon—carbon bond; and $R^g$ is a hydrogen atom or a methyl group.

The invention provides, in another aspect, a polymer including a structural unit shown by the following formula (9):

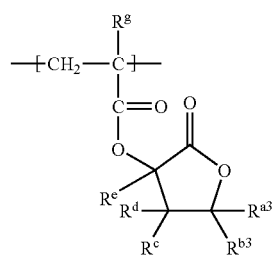

(9)

wherein each of $R^{a3}$ and $R^{b3}$ is, identical to or different from each other, a hydrogen atom, a hydrocarbon group, or a heterocyclic group, where $R^{a3}$ and $R^{b3}$ may be combined to form a ring with the adjacent carbon atom; each of $R^c$, $R^d$, and Re is, identical to or different from one another, a hydrogen atom or an organic group, where $R^c$, $R^d$, and $R^e$ may be combined to form a ring with the adjacent carbon atom or carbon—carbon bond; and $R^g$ is a hydrogen atom or a methyl group.

In addition, the invention provides a photosensitive resinous composition. The composition includes the polymer just mentioned above and a light-activatable acid generator.

In a further aspect, the invention provides a γ-butyrolactone derivative shown by the following formula (10):

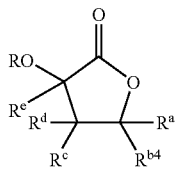
(10)

wherein R is a hydrogen atom or a (meth)acryloyl group; each of $R^a$, $R^c$, $R^d$, and $R^e$ is, identical to or different from one another, a hydrogen atom or an organic group; and $R^{b4}$ is a bridged cyclic hydrocarbon group, where $R^c$, $R^d$, and $R^e$ may be combined to form a ring with the adjacent carbon atom or carbon—carbon bond.

In this γ-butyrolactone derivative, the bridged cyclic hydrocarbon group may be a bicyclic or tricyclic bridged hydrocarbon group. The bridged ring in the bridged cyclic hydrocarbon group includes, but is not limited to, an adamantane ring, a perhydroindene ring, a decalin ring, a perhydrofluorene ring, a perhydroanthracene ring, a perhydrophenanthrene ring, a tricyclo[5.2.1.0$^{2,6}$]decane ring, a perhydroacenaphthene ring, a perhydrophenalene ring, a norbornane ring, and a norbornene ring.

Further, the invention provides a process for producing a conjugated unsaturated compound. This process includes the step of allowing (A12) an alcohol shown by the following formula (2a):

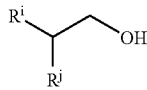
(2a)

wherein each of $R^i$ and $R^j$ is, identical to or different from each other, a hydrogen atom or an organic group, where $R^i$ and $R^j$ may be combined to form a ring with the adjacent carbon atom, to react with (B13) an active olefin shown by the following formula (3a):

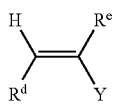
(3a)

wherein each of $R^d$ and $R^e$ is, identical to or different from each other, a hydrogen atom or an organic group; and Y is an electron attracting group, where $R^d$, $R^e$ and Y may be combined to form a ring with the adjacent carbon atom or carbon—carbon bond, in the presence of molecular oxygen by catalysis of the imide compound of the formula (1) to yield a conjugated unsaturated compound shown by the following formula (11):

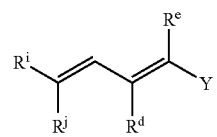
(11)

wherein $R^d$, $R^e$, $R^i$, $R^j$, and Y have the same meanings as defined above.

In the aforementioned process for producing an organic compound, when (A13) an acetal shown by the following formula (12):

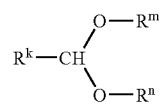
(12)

wherein each of $R^k$, $R^m$, and $R^n$ is, identical to or different from one another, a hydrogen atom or an organic group, where $R^m$ and $R^n$ may be combined to form a ring with the adjacent two oxygen atoms and the carbon atom indicated in the formula, is allowed to react with (B11) the active olefin of the formula (3) in the presence of molecular oxygen by catalysis of the imide compound of the formula (1), a β-hydroxyacetal compound shown by the following formula (13):

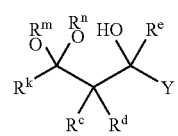
(13)

wherein $R^c$, $R^d$, $R^e$, $R^k$, $R^m$, $R^n$, and Y have the same meanings as defined above, can be obtained.

In the process for producing an organic compound, (A31) a compound having a methine carbon atom and being shown by the following formula (14):

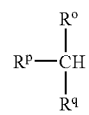
(14)

wherein each of $R^o$, $R^p$, and $R^q$ is, identical to or different from one another, an organic group, where $R^o$, $R^p$, and $R^q$ may be combined to form a ring with the adjacent carbon atom, may be allowed to react with (B11) the active olefin of the formula (3) in the presence of molecular oxygen by catalysis of the imide compound of the formula (1), to yield at least one hydroxy compound selected from the following formulae (15) and (16):

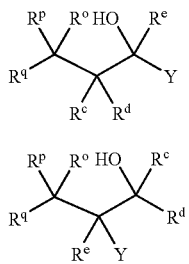

(15)

(16)

wherein $R^c$, $R^d$, $R^e$, $R^o$, $R^p$, $R^q$, and Y have the same meanings as defined above.

In the process for producing an organic compound, (A31) the compound of the formula (14) having a methine carbon atom may be allowed to react with (B14) an active olefin shown by the following formula (3b):

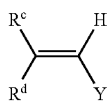

(3b)

wherein each of $R^c$ and $R^d$ is, identical to or different from each other, a hydrogen atom or an organic group; and Y is an electron attracting group, where $R^c$, $R^d$, and Y may be combined to form a ring with the adjacent carbon atom or carbon—carbon bond, in the presence of molecular oxygen by catalysis of the imide compound of the formula (1), to yield a carbonyl compound shown by the following formula (17):

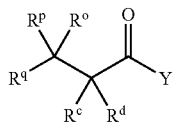

(17)

Wherein $R^c$, $R^d$, $R^o$, $R^p$, $R^q$, and Y have the same meanings as defined above.

In addition and advantageously, the invention provides a process for producing a compound having an electron attracting group. This process includes the step of allowing (A31) the compound of the formula (14) having a methine carbon atom to react with (B15) an active olefin shown by the following formula (3c):

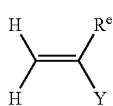

(3c)

wherein $R^e$ is a hydrogen atom or an organic group; and Y is an electron attracting group, in the presence of molecular oxygen by catalysis of the imide compound of the formula (1), to yield an organic compound shown by the following formula (18):

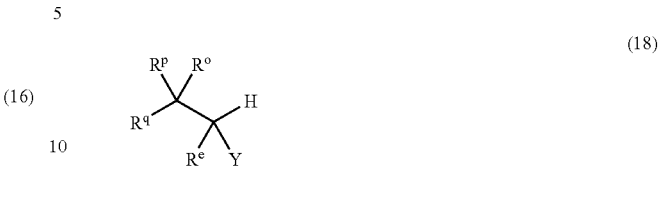

(18)

wherein $R^e$, $R^o$, $R^p$, $R^q$ and Y have the same meanings as defined above.

Further in the process for producing an organic compound, (A11) the alcohol of the formula (2) may be allowed to react with (B21) the compound of the formula (14) having a methine carbon atom in the presence of molecular oxygen by catalysis of the imide compound of the formula (1), to yield an alcohol shown by the following formula (19):

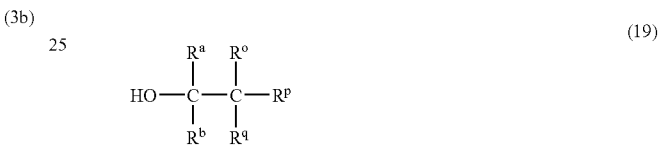

(19)

wherein $R^a$, $R^b$, $R^o$, $R^p$, and $R^q$ have the same meanings as defined above.

In addition, in the process for producing an organic compound, (A32) a compound having a methine carbon atom and shown by the following formula (14a):

(14a)

wherein each of $R^{o1}$, $R^{p1}$ and $R^{q1}$ is, identical to or different from one another, an organic group, where $R^{o1}$, $R^{p1}$ and $R^{q1}$ may be combined to form a ring with the adjacent carbon atom, may be allowed to react with (B22) a compound having a methine carbon atom and shown by the following formula (14b):

(14b)

wherein each of $R^{o2}$, $R^{p2}$ and $R^{q2}$ is, identical to or different from one another, an organic group, where $R^{o2}$, $R^{p2}$ and $R^{q2}$ may be combined to form a ring with the adjacent carbon atom, in the presence of molecular oxygen by catalysis of the imide compound of the formula (1), to yield a coupling product shown by the following formula (20):

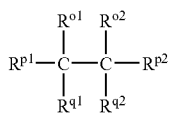
(20)

wherein $R^{o1}$, $R^{p1}$, $R^{q1}$, $R^{o2}$, $R^{p2}$ and $R^{q2}$ have the same meanings as defined above.

A metallic compound can be used as a co-catalyst in the production process of an organic acid, the production process of an α-hydroxy-γ-butyrolactone derivative, the production process of a conjugated unsaturated compound, and the production process of a compound having an electron attracting group.

The term "organic group" in the present description is used in a wide meaning and includes not only carbon-atom-containing groups but also, for example, a halogen atom, a hydroxyl group, a mercapto group, an amino group, a nitro group, a sulfonic acid group, and other groups each containing a non-metallic atom.

BEST MODE FOR CARRYING OUT THE INVENTION

[Imide Compound]

The imide compounds of the formula (1) are used as catalysts in the invention. Of the substituents $R^1$ and $R^2$ in the imide compounds, the halogen atom includes iodine, bromine, chlorine and fluorine. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each having about 1 to 10 carbon atoms. Preferred alkyl groups are alkyl groups each having about 1 to 6 carbon atoms, and are typically preferably lower alkyl groups each having about 1 to 4 carbon atoms.

The aryl group includes phenyl, and naphthyl groups, for example. Illustrative cycloalkyl groups include cyclopentyl, and cyclohexyl groups. Illustrative alkoxy groups are methoxy, ethoxy, propoxy, isopropoxy, butoxy, isobutoxy, t-butoxy, pentyloxy, hexyloxy, and other alkoxy groups each having about 1 to 10 carbon atoms, and preferably having about 1 to 6 carbon atoms. Among them, lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, and are especially lower alkoxycarbonyl groups each having about 1 to 4 carbon atoms in the alkoxy moiety.

The illustrative acyl groups include, for example, formyl, acetyl, propionyl, butyryl, isobutyryl, valeryl, isovaleryl, pivaloyl, and other acyl groups each having about 1 to 6 carbon atoms.

The substituents $R^1$ and $R^2$ may be identical to or different from each other. The substituents $R^1$ and $R^2$ in the formula (1) may be combined to form a double bond, or an aromatic or non-aromatic ring. The preferred aromatic or non-aromatic ring is a 5- to 12-membered ring, and especially a 6- to 10-membered ring. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (1), X represents an oxygen atom or a hydroxyl group, and the bond between the nitrogen atom N, and X is a single bond or a double bond.

To $R^1$, $R^2$, or to the double bond or aromatic or non-aromatic ring formed together by $R^1$ and $R^2$, one or two N-substituted cyclic imido groups indicated in the formula (1) may be further bonded. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

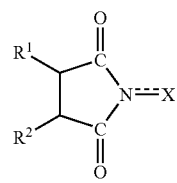
(1a)

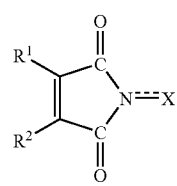
(1b)

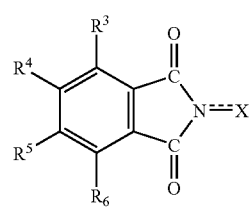
(1c)

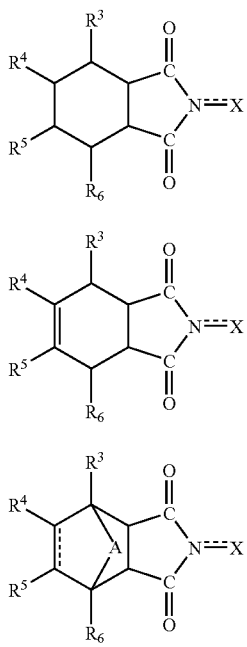

wherein R³ to R⁶ are each, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where, adjacent groups of R³ to R⁶ may be combined to form an aromatic or non-aromatic ring; in the formula (1f), A is a methylene group or an oxygen atom, and R¹ and R² have the same meanings as defined above, where one or two N-substituted cyclic imido groups indicated in the formula (1c) may be further bonded to the benzene ring in the formula (1c); and X has the same meanings as defined above.

In the substituents R³ to R⁶, the alkyl group includes similar alkyl groups to those exemplified above, especially alkyl groups each having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. The acyl group includes similar acyl groups to those described above, especially acyl groups each having about 1 to 6 carbon atoms. The illustrative halogen atoms include fluorine, chlorine and bromine atoms. Each of the substituents R³ to R⁶ is often a hydrogen atom, a lower alkyl group having about 1 to 4 carbon atoms, a carboxyl group, a nitro group, or a halogen atom. The ring formed together by R³ to R⁶ includes similar rings to the aforementioned rings which are formed together by R¹ and R². Among them, aromatic or non-aromatic 5- to 12-membered rings are particularly preferred.

Illustrative preferred imide compounds include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds of the formula (1) can be prepared by a conventional imidation process (a process for the formation of an imide), such as a process that comprises the steps of allowing a corresponding acid anhydride to react with hydroxylamine NH₂OH for ring-opening of an acid anhydride group, and closing the ring to form an imide.

Such acid anhydrides include succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds of the formula (1) can be used alone or in combination. The imide compounds can be used as being supported by a carrier. As such carriers, activated carbon, zeolite, silica, silica-alumina, bentonite, and other porous carries are frequently employed.

The proportion of the imide compound can be selected within a wide range, and is, for example, from about 0.0001 to 1 mole, preferably from about 0.001 to 0.5 mole, and more preferably from about 0.01 to 0.4 mole, relative to 1 mole of the compound that is used in a less proportion between the compound (A) which is capable of forming a stable radical and the radical scavenging compound (B). The imide compound is frequently used in a proportion ranging from about 0.05 to 0.35 mole.

[Promoter (Co-catalyst)]

In the inventive process, a metallic compound as a promoter (co-catalyst) can be used in combination with the imide compound. The combination use of the imide compound with the metallic compound can improve or enhance the rate and selectivity of a reaction.

Metallic elements for constituting such metallic compounds are not critical and can be any of metallic elements of the Groups 1 to 15 of the Periodic Table of Elements. The term "metallic element" as used herein also includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), and Group 15 elements (e.g., Sb, Bi). Preferred metallic elements include transition metal elements (elements of Groups 3 to 12 of the Periodic Table of Elements). Among them, elements of the Groups 5 to 11, especially elements of Groups 6, 7 and 9 of the Periodic Table of Elements are preferred, of which V, Mo, Co and Mn are typically preferred. The valence of the metallic element is not critical, and is about 0 to 6 in many cases.

The metallic compounds include, but are not limited to, elementary substances, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of the aforementioned metallic elements; salts of organic acids (e.g., salts of acetic acid, propionic acid, hydrocyanic acid, naphthenic acid, and stearic acid), complexes, and other organic compounds of the metallic elements. Ligands constituting the complexes include OH (hydroxo), alkoxy (e.g., methoxy, ethoxy, propoxy, and butoxy), acyl (e.g., acetyl, and propionyl), alkoxycarbonyl (e.g., methoxycarbonyl, and ethoxycarbonyl), acetylacetonato, cyclopentadienyl group, halogenatoms (e.g., chlorine and bromine), CO, CN, oxygen atom, $H_2O$ (aquo), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compounds include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Illustrative vanadium compounds include vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of 2 to 5. Illustrative molybdenum compounds include molybdenum hydroxide, molybdenum oxide, molybdenum chloride, molybdenum bromide, molybdenum sulfide, molybdic acid or its salts, phosphomolybdic acid or its salts, silicomolybdic acid or its salts, and other inorganic compounds; molybdenum carbonyl, bis(acetylacetonato)dioxomolybdenum, chlorotricarbonyl(η-cyclopentadienyl)molybdenum, dibromobis(η-cyclopentadienylmolybdenum, and other complexes, and other molybdenum compounds having a valence of 0 to 6. Examples of compounds of the other metallic elements include compounds corresponding to the above-mentioned cobalt, vanadium or molybdenum compounds. Each of the metallic compounds can be used alone or in combination. Particularly, the combination use of a divalent metallic compound (e.g., a divalent cobalt compound) with a trivalent metallic compound (e.g., a trivalent cobalt compound) can increase the yield and selectivity of a target compound.

The proportion of the metallic compound is, for example, about 0.0001 to 0.7 mole, preferably about 0.001 to 0.5 mole, more preferably about 0.002 to 0.1 mole, and frequently about 0.005 to 0.05 mole, relative to 1 mole of the compound that is used in a less proportion between the compound (A) and the compound (B).

[Oxygen and Radical Generator]

As the oxygen, either of molecular oxygen and nascent oxygen can be used. Such molecular oxygen includes, but is not limited to, pure oxygen, and oxygen diluted with an inert gas such as nitrogen, helium, argon or carbon dioxide. Air is preferably used as the molecular oxygen from the viewpoints of operating properties and safety, as well as cost efficiency. The oxygen may be used in an excess molar ratio relative to the compound, between compound (A) and compound (B), that is used in a lesser proportion.

The term "radical generator" for use in the invention is employed in a wide range of meanings and includes any substances that are capable of forming a radical (>NO.) on an oxygen atom bonded to a nitrogen atom of the imide compound. Such radical generators include, but are not limited to, halogens (e.g., iodine, bromine, and chlorine), peroxides, and other radical initiators; carbon monoxide, nitrogen oxides, sulfur oxides, and other oxygen-atom-containing gases (oxidizing gases); electrodes; aldehydes and other precursors of peroxides. The metallic compounds can be also classified as radical generators. Each of these radical generators can be used alone or in combination. The amount of the radical generator may be a catalytic amount, but may be excess moles relative to the compound that is used in a less proportion between the compound (A) and the compound (B).

Either or both of the oxygen and the radical generator may be used.

[Compound (A) Capable of Forming Stable Radical]

The compounds (A) capable of forming a stable radical include (A1) oxygen-atom-containing compounds each having a carbon-hydrogen bond at the adjacent position to an oxygen atom, (A2) carbonyl-group-containing compounds, and (A3) compounds each having a hydrocarbon group with a methine carbon atom. Each of these compounds can be used alone or in combination. These compounds may have various substituents within a range not adversely affecting the reaction. The compound (A) capable of forming a stable radical serves as a radical donating compound in the reaction in question.

The oxygen-atom-containing compounds (A1) each having a carbon-hydrogen bond at the adjacent position to an oxygen atom include, but are not limited to, (A1–1) primary or secondary alcohols, (A1–2) ethers each having a carbon-hydrogen bond at the adjacent position to an oxygen atom, and (A1–3) acetals (including hemiacetals) each having a carbon-hydrogen bond at the adjacent position to an oxygen atom.

The primary or secondary alcohols (A1–1) include a wide variety of alcohols. Such alcohols may be any of monohydric alcohols, dihydric alcohols or polyhydric alcohols.

Illustrative primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, hexamethylene glycol, pentaerythritol, and other saturated or unsaturated aliphatic primary alcohols each having about 1 to 30 (preferably about 1 to 20, and more preferably about 1 to 15) carbon atoms; cyclopentylmethyl alcohol, cyclohexylmethyl alcohol, 2-cyclohexylethyl alcohol, and other saturated or unsaturated alicyclic primary alcohols; benzyl alcohol, 2-phenylethyl alcohol, 3-phenylpropyl alcohol, cinnamic alcohol, and other aromatic primary alcohols; and 2-hydroxymethylpyridine, and other heterocyclic alcohols.

Typical secondary alcohols include, but are not limited to, 2-propanol, s-butyl alcohol, 2-pentanol, 3-pentanol, 3,3-dimethyl-2-butanol, 2-octanol, 4-decanol, 2-hexadecanol, 2-penten-4-ol, 1,2-propanediol, 2,3-butanediol, 2,3-pentanediol, and other vicinal diols, and other saturated or unsaturated aliphatic secondary alcohols each having about 3 to 30 (preferably about 3 to 20, and more preferably about 3 to 15) carbon atoms; 1-cyclopentylethanol, 1-cyclohexylethanol, and other secondary alcohols each having an aliphatic hydrocarbon group and an alicyclic hydrocarbon (e.g., a cycloalkyl group) bonded to a carbon atom, to which carbon atom a hydroxyl group is bonded; cyclobutanol, cyclopentanol, cyclohexanol, cyclooctanol, cyclododecanol, 2-cyclohexen-1-ol, 2-adamantanol, 2-adamantanol having 1 to 4 hydroxyl groups at the bridgehead positions, 2-adamantanol having an oxo group on an adamantane ring, and other saturated or unsaturated alicyclic secondary alcohols (including bridged cyclic secondary alcohols) each having about 3 to 20 members (preferably about 3 to 15 members, more preferably about 5 to 15 members, and typically 5 to 8 members); 1-phenylethanol, 1-phenylpropanol, 1-phenylmethylethanol, diphenylmethanol, and other aromatic secondary alcohols; and 1-(2-pyridyl)ethanol, and other heterocyclic secondary alcohols.

Typical alcohols further include, for example, 1-adamantanemethanol, α-methyl-1-adamantanemethanol, α-ethyl-1-adamantanemethanol, α-isopropyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4a-decalinmethanol, 8a-hydroxy-α-methyl-4a-decalinmethanol, α-methyl-4a-perhydrofluorenemethanol, α-methyl-4a-perhydroanthracenemethanol, α-methyl-8a-perhydrophenanthrenemethanol, α-methyl-2-tricyclo[5.2.1.0$^{2,6}$]decanemethanol, 6-hydroxy-α-methyl-2-tricyclo[5.2.1.0$^{2,6}$]decanemethanol, α-methyl-2a-perhydroacenaphthenemethanol, α-methyl-3a-perhydrophenalenemethanol, α-methyl-1-norbornanemethanol, α-methyl-2-norbornene-1-methanol, and other alcohols each having a bridged cyclic hydrocarbon group, such as compounds each having a bridged cyclic hydrocarbon group bonded to a carbon atom, to which carbon atom a hydroxyl group is bonded.

Preferred alcohols include secondary alcohols and the alcohols each having a bridged cyclic hydrocarbon group. Such secondary alcohols include 2-propanol, s-butyl alcohol, and other aliphatic secondary alcohols; 1-cyclohexyl ethanol, and other secondary alcohols each having an aliphatic hydrocarbon group (e.g., a $C_1$–$C_4$ alkyl group, or a $C_6$–$C_{14}$ aryl group) and a non-aromatic carbocyclic group (e.g., a $C_3$–$C_{15}$ cycloalkyl group or a cycloalkenyl group) bonded to a carbon atom, to which carbon atom a hydroxyl group is bonded; cyclopentanol, cyclohexanol, 2-adamantanol, and other alicyclic secondary alcohols each having about 3 to 15 members; 1-phenylethanol, and other aromatic secondary alcohols.

The ethers (A1–2) each having a carbon-hydrogen bond at the adjacent position to an oxygen atom include, but are not limited to, dimethyl ether, diethyl ether, dipropyl ether, diisopropyl ether, dibutyl ether, methyl ethyl ether, methyl butyl ether, ethyl butyl ether, diallyl ether, methyl vinyl ether, ethyl allyl ether, and other aliphatic ethers; anisole, phenetole, dibenzyl ether, phenyl benzyl ether, and other aromatic ethers; and tetrahydrofuran, and other cyclic ethers.

The acetals (A1–3) each having a carbon-hydrogen bond at the adjacent position to an oxygen atom include, for example, acetals derived from aldehydes and alcohols or acid anhydrides. Such acetals include cyclic acetals and acyclic acetals. The aldehydes include, but are not limited to, formaldehyde, acetaldehyde, propionaldehyde, butyraldehyde, isobutyraldehyde, pentanal, hexanal, decanal, and other aliphatic aldehydes; cyclopentanecarbaldehyde, cyclohexanecarbaldehyde, and other alicyclic aldehydes; benzaldehyde, phenylacetaldehyde, and other aromatic aldehydes. The alcohols include, but are not limited to, methanol, ethanol, 1-propanol, 1-butanol, benzyl alcohol, and other monohydric alcohols; ethylene glycol, propylene glycol, 1,3-propanediol, 2,2-dibromo-1,3-propanediol, and other dihydric alcohols. Typical acetals are, for example, 1,3-dioxolane, 2-methyl-1,3-dioxolane, 2-ethyl-1,3-dioxolane, and other 1,3-dioxolane compounds; 2-methyl-1,3-dioxane, and other 1,3-dioxane compounds; acetaldehyde dimethyl acetal, and other dialkyl acetal compounds.

The compounds (A2) each containing a carbonyl group include, but are not limited to, acetone, methyl ethyl ketone, 3-pentanone, acetophenone, and other chain ketones; cyclopentanone, cyclohexanone, and other cyclic ketones; biacetyl (2,3-butanedione), 2,3-pentanedione, 3,4-hexanedione, bibenzoyl (benzil), acetylbenzoyl, cyclopentane-1,2-dione, cyclohexane-1,2-dione, and other 1,2-dicarbonyl compounds (e.g., α-diketones); acetoin, benzoin, and other α-keto-alcohols; acetaldehyde, propionaldehyde, butanal, hexanal, and other aliphatic aldehydes; cyclohexyl aldehyde, and other alicyclic aldehyde; benzaldehyde, and other aromatic aldehydes. Preferred carbonyl-group-containing compounds are chain ketones, 1,2-dicarbonyl compounds (e.g., α-diketones), α-keto-alcohols, and other ketones.

The compounds (A3) each having a hydrocarbon group with a methine carbon atom include (A3–1) cyclic compounds each having a methine group (i.e., a methine carbon-hydrogen bond) as a structural unit of a ring, and (A3–2) chain compounds each having a methine carbon atom.

The cyclic compounds (A3–1) include, for example, (A3–1a) bridged cyclic compounds having at least one methine group, and (A3–1b) non-aromatic cyclic compounds (e.g., alicyclic hydrocarbons) each having a hydrocarbon group bonded to a ring. The bridged cyclic compounds also include compounds in which two rings possess two carbon atoms in common, such as hydrogenated products of condensed polycyclic aromatic hydrocarbons.

The bridged cyclic compounds (A3–1a) include, but are not limited to, decalin, bicyclo[2.2.0]hexane, bicyclo[2.2.2]octane, bicyclo[3.2.1]octane, bicyclo[4.3.2]undecane, bicyclo[3.3.3]undecane, thujone, carane, pinane, pinene, bornane, bornylene, norbornane, norbornene, camphor, camphoric acid, camphene, tricyclene, tricyclo[5.2.1.0$^{3,8}$]decane, tricyclo[4.2.1.1$^{2,5}$]decane, exotricyclo[5.2.1.0$^{2,6}$]decane, endotricyclo[5.2.1.0$^{2,6}$]decane, tricyclo[4.3.1.1$^{2,5}$]undecane, tricyclo[4.2.2.1$^{2,5}$]undecane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$]dodecane, perhydroanthracene, perhydroacenaphthene, perhydrophenanthrene, perhydrophenalene, perhydroindene, quinuclidine, and other bridged cyclic hydrocarbons or bridged heterocyclic compounds each having 2 to 4 rings, and derivatives thereof. These bridged cyclic compounds each have a methine carbon atom at a bridgehead position (corresponding to a junction position when two rings commonly possess two atoms).

The non-aromatic cyclic compounds (A3–1b) each having a hydrocarbon group bonded to a ring include, but are not limited to, 1-methylcyclopentane, 1-methylcyclohexane, limonene, menthene, menthol, carbomenthone, menthone, and other alicyclic hydrocarbons each having about 3 to 15 members and a hydrocarbon group (e.g., an alkyl group) bonded to its ring, and their derivatives. The hydrocarbon group just mentioned above contains about 1 to 20 (preferably 1 to 10) carbon atoms. The non-aromatic cyclic compounds (A3–1b) each having a hydrocarbon group bonded to its ring have a methine carbon atom at the bonding site between the ring and the hydrocarbon group.

The chain compounds (A3–2) each having a methine carbon atom include, but are not limited to, chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having about 4 to 20 (preferably 4 to 10) carbon atoms, and derivatives thereof.

[Radical scavenging Compound (B)]

The radical scavenging compounds (B) include (B1) unsaturated compounds, (B2) compounds each having a hydrocarbon group with a methine carbon atom, and (B3) heteroatom-containing compounds. Each of these compounds may be used alone or in combination. These compounds may have various substituents within a range not adversely affecting the reaction.

The unsaturated compounds (B1) include a wide variety of compounds each having an unsaturated bond. Such compounds include, for example, (B1–1) unsaturated compounds each having an electron attracting group at the adjacent position of a carbon—carbon unsaturated bond [active olefins (electron-deficient olefins) and other active unsaturated compounds], (B1–2) compounds each having a carbon—carbon triple bond, (B1–3) compounds each having an aromatic ring, (B1–4) ketenes, and (B1–5) isocyanate or thioisocyanate compounds.

The active unsaturated compounds (B1–1) include, but are not limited to, methyl (meth)acrylate, ethyl (meth) acrylate, isopropyl (meth)acrylate, phenyl (meth)acrylate, methyl crotonate, ethyl crotonate, methyl 3-methyl-2-butenoate, ethyl 3-methyl-2-butenoate, methyl 2-pentenoate, methyl 2-octenoate, and other $\alpha,\beta$-unsaturated esters; vinyl methyl ketone, vinyl ethyl ketone, methyl 1-propenyl ketone, and other $\alpha,\beta$-unsaturated ketones; propenal, crotonaldehyde, and other $\alpha,\beta$-unsaturated aldehydes; acrylonitrile, methacrylonitrile, and other $\alpha,\beta$-unsaturated nitrites; (meth)acrylic acid, crotonic acid, and other $\alpha,\beta$-unsaturated carboxylic acids; (meth)acrylamide, and other $\alpha,\beta$-unsaturated carboxylic acid amides; N-(2-propenylidene)methylamine, N-(2-butenylidene)methylamine, and other $\alpha,\beta$-unsaturated imines; styrene, vinyltoluene, $\alpha$-methylstyrene, $\beta$-methylstyrene, and other styrene derivatives, and other compounds each having an aryl group bonded at the adjacent position to a carbon—carbon unsaturated bond; butadiene, isoprene, 2-chlorobutadiene, 2-ethylbutadiene, vinylacetylene, cyclopentadiene derivatives, and other conjugated dienes (including compounds in which a double bond and a triple bond are conjugated).

The compounds (B1–2) each having a carbon—carbon triple bond include, for example, methylacetylene, and 1-butyne. The compounds (B1–3) each having an aromatic ring include, for example, compounds each having a benzene ring, a naphthalene ring, or another aromatic carbon ring; and compounds each having a pyrrole ring, a furan ring, a thiophene ring, or another aromatic heterocycle. The ketenes (B1–4) include, for example, ketene, and 2-methylketene. The isocyanate or thioisocyanate compounds (B1–5) include, for example, methyl isocyanate, ethyl isocyanate, phenyl isocyanate, methyl thioisocyanate, ethyl thioisocyanate, and phenyl thioisocyanate.

The compounds (B2) each having a hydrocarbon group with a methine carbon atom include, for example, the compounds exemplified as the compounds (A3). The same compound can be used as the compound (A3) and the compound (B2) in the reaction.

The heteroatom-containing compounds (B3) include, for example, (B3–1) compounds each having a sulfur atom, (B3–2) compounds each having a nitrogen atom, (B3–3) compounds each having a phosphorus atom, and (B3–4) compounds each having an oxygen atom. The compounds (B3–1) each having a sulfur atom include, for example, sulfides and thiols. The compounds (B3–2) each having a nitrogen atom include, for example, amines. The compounds (B3–3) each having a phosphorus atom include, for example, phosphates. The compounds (B3–4) each having an oxygen atom include, for example, N-oxides.

In the present invention, when a 1,2-dicarbonyl compound or its hydroxy reductant is used as the compound (A), a radical scavenging compound selected from the compounds (B1) and (B3) should be used as the compound (B). Such 1,2-dicarbonyl compounds include 1,2-dicarbonyl compounds (e.g., $\alpha$-diketones) exemplified as the carbonyl-group-containing compounds (A2). Hydroxy reductants of 1,2-dicarbonyl compounds include $\alpha$-keto-alcohols exemplified as the carbonyl-group-containing compounds (A2), and vicinal diols exemplified as the primary or secondary alcohols (A1–1).

A reaction between the compound (A) capable of forming a stable radical with the radical scavenging compound (B) is generally performed in an organic solvent. Such organic solvents include, but are not limited to, acetic acid, propionic acid, and other organic acids; acetonitrile, propionitrile, benzonitrile, and other nitriles; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitriles, trifluoromethylbenzene, and other halogenated hydrocarbons, ethyl acetate and other esters are used as the solvents.

The proportion of the compound (A) capable of forming a stable radical to the radical scavenging compound (B) can be appropriately selected according to the types (costs, reactivity) or combination of the both compounds. For example, the compound (A) can be used in excess amounts (e.g., about 2 to 50 times by mole) relative to the compound (B), or vice versa, the compound (B) can be used in excess amounts to the compound (A).

According to the invented process, the reaction can smoothly proceed even under relatively mild conditions. A reaction temperature can be appropriately selected according to the types of the compound (A) and the compound (B) and type of a target product, and is, for example, about 0° C. to 300° C., preferably about 20° C. to 200° C., more preferably about 30° C. to 150° C. The reaction is frequently performed at a temperature of about 40° C. to 100° C. The reaction can be carried out at atmospheric pressure or under a pressure (under a load). When the reaction is conducted under a pressure, the pressure is usually about 1 to 100 atm (e.g. 1.5 to 80 atm), preferably about 2 to 70 atm. A reaction time can be appropriately selected within a range of, for example, 30 minutes to 48 hours depending on the reaction temperature and pressure.

The reaction can be performed in a batch system, a semi-batch system, a continuous system or other conventional manners. After the completion of the reaction, reaction products can be easily separated and purified by a conventional technique, such as filtration, concentration, distillation, extraction, crystallization, recrystallization, column chromatography, and other separation means, or any combination of these separation means.

According to the invented process, an addition or substitution reaction product is formed corresponding to a combination of the compound (A) capable of forming a stable radical and the radical scavenging compound (B).

For example, when the oxygen-atom-containing compound (A1) having a carbon-hydrogen bond at the adjacent position to an oxygen atom is employed as the compound (A), the adjacent position to the oxygen atom is bonded to an atom (e.g., a carbon atom) constituting an unsaturated bond of the unsaturated compound (B1), to the methine carbon atom of the compound (B2) having a hydrocarbon group with a methine carbon atom, or to the heteroatom of the heteroatom-containing compound (B3). Thus, an addition or substitution reaction product is obtained.

When the carbonyl-group-containing compound (A2) is employed as the compound (A), a bond between a carbonyl group and an atom adjacent to the carbonyl group is broken, and an atomic group containing the carbonyl group (e.g., an acyl group) is bonded to the aforementioned position of the compound (B1), (B2) or (B3) toyieldanadditionorsubstitutionreaction product. When the compound (A3) containing a hydrocarbon group with a methine carbon atom is employed as the compound (A) capable of forming a stable radical, the methine carbon atom is bonded to the aforementioned position of the compound (B1), (B2) or (B3) to yield an addition or substitution reaction product.

Generally, the use of the unsaturated compound (B1) as the radical scavenging compound (B) will yield an addition reaction product, and the use of the compound (B2) having a hydrocarbon group with a methine carbon atom as the compound (B) will yield a substitution reaction product (e.g., a coupling product).

According to the invented process, an oxidized product of the addition or substitution reaction product can be formed. For example, when the reaction is performed in the presence of oxygen using the unsaturated compound (B1) as the radical scavenging compound (B), a group derived from the compound (A) is bonded to one carbon atom of the two carbon atoms constituting the unsaturated bond as mentioned above, and a hydroxyl group can be introduced to the other carbon atom.

A reaction mechanism is not clarified in detail, but is supposed as follows. The radical generator or oxygen acts upon the imide compound, and a free radical is formed on an oxygen atom bonded to a nitrogen atom of the imide compound. This radical abstracts a hydrogen from the compound (A), and of the compound (A), a free radical is then generated on a carbon atom at the adjacent position to an oxygen atom in the compound (A1), on a carbonyl carbon atom in the compound (A2), or on the methine carbon atom in the compound (A3). This radical attacks an atom constituting an unsaturated bond, the methine carbon atom, or the heteroatom of the compound (B). Subsequently, the above oxidation proceeds under some conditions.

The addition or substitution reaction product formed through the above reaction, or the oxidized product formed through oxidation of the reaction product may further undergo, for example, a dehydration reaction, cyclization reaction, decarboxylation reaction, rearrangement reaction, or isomerization in a reaction system, depending on the structure of the product, to yield a corresponding organic compound.

The reaction of the compound (A) capable of forming a stable radical with the radical scavenging compound (B) should be preferably conduced under conditions with minimal polymerization inhibitors (e.g., hydroquinone). For example, the proportion of the polymerization inhibitor in the reaction system should be preferably 1000 ppm or less, and more preferably 100 ppm or less. If the proportion of the polymerization inhibitor exceeds 1000 ppm, a reaction rate is liable to decrease, and the imide compound of the formula (1) and/or the co-catalyst has to be used in large amounts in some cases. In contrast, when the proportion of the polymerization inhibitor in the reaction system is small, the reaction rate increases to improve a yield, and the reaction results have a high reproducibility to stably yield a target compound. The unsaturated compounds (B1) or other compounds for use in commercial, to which a polymerization inhibitor is added, should be preferably subjected to elimination of the polymerization inhibitor by, for example, distillation, prior to the reaction. The same goes for any reaction in which the compound (A) is allowed to react with the compound (B) in the presence of the imide compound.

According to the invention, a variety of organic compounds as shown below can be obtained by allowing an appropriate combination of the compound (A) capable of forming a stable radical with the radical scavenging compound (B) to react with each other.

1. Production of 2,3-Dihydroxy Compound

A first embodiment of the productions will be described below. When the alcohol of the formula (2) is allowed to react with the active olefin of the formula (3) in the presence of molecular oxygen by catalysis of the imide compound of the formula (1), the 1,3-dihydroxy compound of the formula (4) is formed.

The organic group in $R^a$ and $R^b$ in the formula (2) has only to be an organic group that does not adversely affect the reaction (e.g., an organic group that is not reactive under reaction conditions according to the process). Such organic groups include, for example, hydrocarbon groups and heterocyclic groups.

The hydrocarbon groups include aliphatic hydrocarbon groups, alicyclic hydrocarbon groups, and aromatic hydrocarbon groups. Such aliphatic hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups, and alkynyl groups) each having about 1 to 20 (preferably about 1 to 10, and more preferably about 1 to 6) carbon atoms.

The alicyclic hydrocarbon groups include, but are not limited to, cyclopropyl, cyclobutyl, cyclopentyl, cyclohexyl, cyclohexenyl, cyclooctyl, cyclodecyl, cyclododecyl, and other monocyclic alicyclic hydrocarbon groups (e.g., cycloalkyl groups and cycloalkenyl groups) each having about 3 to 20 carbon atoms (preferably having about 3 to 15 carbon atoms); and bridged cyclic hydrocarbon groups.

Such bridged cyclic hydrocarbon groups include bicyclic, tricyclic or tetracyclic bridged hydrocarbon groups, of which bicyclic or tricyclic bridged hydrocarbon groups are preferred. Illustrative bridged rings in the bridged cyclic hydrocarbon groups include, but are not limited to, adamantane ring, perhydroindene ring, decalin ring, perhydrofluorene ring, perhydroanthracene ring, perhydrophenanthrene ring, tricyclo[5.2.1.0$^{2,6}$]decane ring, perhydroacenaphthene ring, perhydrophenalene ring, norbornane ring, and norbornene ring. The bridged cyclic hydrocarbon group may be bonded to a carbon atom to which the hydroxyl group is bonded in the formula through any carbon atom constituting the bridged ring but should be preferably bonded through a carbon atom at a bridgehead position (junction position).

The aromatic hydrocarbon groups include, for example, phenyl, naphthyl, and other aromatic hydrocarbon groups each having about 6 to 14 carbon atoms.

These hydrocarbon groups may have a variety of substituents. Such substituents include, for example, halogen atoms (fluorine, chlorine, bromine, and iodine atoms), oxo group, hydroxyl groups which may be protected by a protective group, amino groups which may be protected by a protective group, amino groups which may be protected by a protective group, carboxyl groups which may be protected by a protective group, substituted oxycarbonyl groups, substituted or unsubstituted carbamoyl groups, nitro group, acyl groups, cyano group, alkyl groups (e.g., methyl, ethyl, and other $C_1$–$C_4$ alkyl groups), cycloalkyl groups, aryl groups (e.g., phenyl, and naphthyl groups), and heterocyclic groups. As the protective groups, conventional protective groups in the field of organic synthesis can be employed.

The protective groups for hydroxyl group and hydroxymethyl group include conventional protective groups. Such protective groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, 1-hydroxyalkyl groups (e.g., 1-hydroxyethyl, 1-hydroxyhexyl, 1-hydroxydecyl, and 1-hydroxyhexadecyl groups), and other groups which are capable of forming an acetal or hemiacetal group with a hydroxyl group; acyl groups (e.g., formyl, acetyl, propionyl, butyryl, isobutyryl, valeryl, pivaloyl, and other $C_1$–$C_6$ aliphatic acyl groups; acetoacetyl group; benzoyl, naphthoyl, and other aromatic acyl groups), alkoxycarbonyl groups (e.g., methoxycarbonyl, ethoxycarbonyl, t-butoxycarbonyl, and other $C_1$–$C_4$-alkoxy-carbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups). When the molecule to be protected has two or more hydroxyl groups (inclusive of hydroxymethyl groups), the protective groups also include divalent hydrocarbon groups (e.g., methylene, ethylidene, isopropylidene, cyclopentylidene, cyclohexylidene, and benzylidene groups) which may have a substituent. Preferred protective groups for hydroxyl group include, for example, $C_1$–$C_4$ alkyl groups; substituted methyl groups, substituted ethyl groups, 1-hydroxyalkyl groups, and other groups that can form an acetal or hemiacetal group with a hydroxyl group; acyl groups, $C_1$–$C_4$ alkoxy-carbonyl groups, substituted or unsubstituted carbamoyl groups, substituted silyl groups, and divalent hydrocarbon groups which may have a substituent.

Protective groups for amino group include the aforementioned alkyl groups, aralkyl groups, acyl groups, alkoxycarbonyl groups, aralkyloxycarbonyl groups, dialkylphosphinothioyl groups, diarylphoshinothioyl groups mentioned as the protective groups for hydroxyl group. Preferred protective groups for amino group are, for example, $C_1$–$C_4$ alkyl groups, $C_1$–$C_6$ aliphatic acyl groups, aromatic acyl groups, and $C_1$–$C_4$ alkoxy-carbonyl groups.

Illustrative protective groups for carboxyl group include, but are not limited to, alkoxy groups (e.g., methoxy, ethoxy, butoxy, and other $C_1$–$C_6$ alkoxy groups), cycloalkyloxy groups, aryloxy groups (e.g., phenoxy group), aralkyloxy groups (e.g., benzyloxy group), trialkylsilyloxy groups (e.g., trimethylsilyloxy group), amino groups which may have a substituent (e.g., amino group; methylamino group, dimethylamino group, and other mono- or di-$C_1$–$C_6$ alkylamino groups), hydrazino group, alkoxycarbonylhydrazino groups, and aralkyloxycarbonylhydrazino groups. Preferred protective groups for carboxyl group are $C_1$–$C_6$ alkoxy groups (especially, $C_1$–$C_4$ alkoxy groups), and mono- or di-$C_1$–$C_6$ alkylamino groups (especially, mono- or di-$C_1$–$C_4$ alkylamino groups).

Heterocyclic rings constituting heterocyclic groups in $R^a$ and $R^b$ include aromatic heterocyclic rings and non-aromatic heterocyclic rings. Such heterocyclic rings include, but are not limited to, heterocyclic rings each containing an oxygen atom as a heteroatom (e.g., furan, tetrahydrofuran, oxazole, isoxazole, and other 5-membered rings, 4-oxo-4H-pyran, tetrahydropyran, morpholine, and other 6-membered rings, benzofuran, isobenzofuran, 4-oxo-4H-chromene, chroman, isochroman, and other condensed rings), heterocyclic rings each containing a sulfur atom as a heteroatom (e.g., thiophene, thiazole, isothiazole, thiadiazole, and other 5-membered rings, 4-oxo-4H-thiopyran, and other 6-membered rings, benzothiophene and other condensed rings), heterocyclic rings each containing a nitrogen atom as a heteroatom (e.g., pyrrole, pyrrolidine, pyrazole, imidazole, triazole, and other 5-membered rings, pyridine, pyridazine, pyrimidine, pyrazine, piperidine, piperazine, and other 6-membered rings, indole, indoline, quinoline, acridine, naphthyridine, quinazoline, purine, and other condensed rings). These heterocyclic groups may have substituents (e.g., similar groups to the substituents that the hydrocarbon groups may have).

The rings formed by $R^a$ and $R^b$ with the adjacent carbon atom include, but are not limited to, cyclopropane, cyclobutane, cyclopentane, cyclopentene, cyclohexane, cyclohexene, cyclooctane, cyclodecane, and cyclododecane rings, decalin ring, adamantane ring, and other non-aromatic carbon rings (cycloalkane rings, cycloalkene rings, and bridged carbon rings) each having about 3 to 20 members (preferably about 3 to 15 members, more preferably about 5 to 15 members, and typically about 5 to 8 members). These rings may have substituents (e.g., similar groups to the substituents that the hydrocarbon groups may have). To these rings, another ring (a non-aromatic ring or an aromatic ring) may be condensed.

Preferred substituent $R^a$ includes hydrogen atom; methyl, ethyl, propyl, isopropyl, butyl, and other $C_1$–$C_4$ alkyl groups, and $C_6$–$C_{14}$ aryl groups. Preferred $R^b$ includes, hydrogen atom, $C_1$–$C_{10}$ aliphatic hydrocarbon groups (e.g., methyl, ethyl, propyl, isopropyl, butyl, isobutyl, s-butyl, t-butyl, pentyl, hexyl, octyl, and decyl groups; particularly $C_1$–$C_{10}$ alkyl groups), and alicyclic hydrocarbon groups (e.g., cyclopentyl, cyclohexyl, cyclohexenyl, and other $C_3$–$C_{15}$ cycloalkyl groups or cycloalkenyl groups; and bridged cyclic hydrocarbon groups). Alternatively, $R^a$ and $R^b$ are preferably combined to form a non-aromatic carbon ring having about 3 to 15 members (particularly about 5 to 8 members) with the adjacent carbon atom.

The alcohols of the formula (2) include, for example, the alcohols exemplified as the primary or secondary alcohols (A1–1).

Preferred alcohols include secondary alcohols (e.g., 2-propanol, s-butyl alcohol, and other aliphatic secondary alcohols; 1-cyclohexylethanol, and other secondary alcohols each having an aliphatic hydrocarbon group (e.g., a $C_1$–$C_4$ alkyl group, or a $C_6$–$C_{14}$ aryl group) and a non-aromatic carbocyclic group (e.g., a $C_3$–$C_{15}$ cycloalkyl group or a cycloalkenyl group) bonded to a carbon atom, to which carbon atom a hydroxyl group is bonded; cyclopentanol, cyclohexanol, 2-adamantanol, and other alicyclic secondary alcohols each having about 3 to 15 members; 1-phenylethanol, and other aromatic secondary alcohols), and alcohols in which the substituent $R^b$ is a bridged cyclic hydrocarbon group.

[Active Olefin]

The organic groups in $R^c$, $R^d$, and $R^e$ in the active olefins of the formula (3) can be any organic groups that do not adversely affect the reaction (e.g., organic groups that are not reactive under reaction conditions according to the invented process). Such organic groups include, but are not limited to, halogen atoms, hydrocarbon groups, heterocyclic groups, substituted oxycarbonyl groups (e.g., alkoxycarbonyl groups, aryloxycarbonyl groups, aralkyloxycarbonyl groups, and cycloalkyloxycarbonyl groups), carboxyl group, substituted or unsubstituted carbamoyl groups (N-substituted or unsubstituted amide groups), cyano group, nitro group, sulfur acid radicals (sulfonic acid groups, and sulfinic acid groups), sulfur acid ester groups (sulfonic acid ester groups, and sulfinic acid ester groups), acyl groups, hydroxyl group, alkoxy groups, and N-substituted or unsubstituted amino groups. The carboxyl group, hydroxyl group, and amino groups may be protected by a conventional protective group.

The halogen atoms include fluorine, chlorine, bromine, and iodine atoms. The hydrocarbon groups include, for example, the groups exemplified as the hydrocarbon groups in $R^a$ and $R^b$. These hydrocarbon groups may have any of the aforementioned substituents. Preferred hydrocarbon groups include, for example, methyl, ethyl, propyl, isopropyl, butyl, isobutyl, s-butyl, t-butyl, vinyl, allyl, and other straight- or branched-chain aliphatic hydrocarbon groups (alkyl groups, alkenyl group, and alkynyl groups) each having about 1 to 6 carbon atoms (particularly about 1 to 4 carbon atoms); phenyl group, naphthyl group, and other aromatic hydrocarbon groups each having about 6 to 14 carbon atoms; cycloalkyl groups; trifluoromethyl group, and other haloalkyl groups each having about 1 to 6 carbon atoms (particularly about 1 to 4 carbon atoms).

The heterocyclic groups include, for example, the groups exemplified as the heterocyclic groups in $R^a$ and $R^b$. These heterocyclic groups may have any of the substituents. The alkoxycarbonyl groups include, but are not limited to, methoxycarbonyl, ethoxycarbonyl, propoxycarbonyl, isopropoxycarbonyl, butoxycarbonyl, t-butoxycarbonyl, and other $C_1$–$C_6$ alkoxy-carbonyl groups. The aryloxycarbonyl groups include, but are not limited to, phenyloxycarbonyl group, and the aralkyloxycarbonyl groups include, for example, benzyloxycarbonyl group. Illustrative cycloalkyloxycarbonyl groups are cyclopentyloxycarbonyl, and cyclohexyloxycarbonyl groups.

The substituted carbamoyl groups include, for example, N-methylcarbamoyl, and N,N-dimethylcarbamoyl groups.

Illustrative sulfonic acid ester groups are methyl sulfonate, ethyl sulfonate, and other sulfonic acid $C_1$–$C_4$ alkyl ester groups. Illustrative sulfinic acid ester groups are methyl sulfinate, ethyl sulfinate, and other sulfinic acid $C_1$–$C_4$ alkyl ester groups. The acyl groups include, but are not limited to, acetyl, propionyl, and other aliphatic acyl groups (e.g., $C_2$–$C_7$ aliphatic acyl groups), and benzoyl, and other aromatic acyl groups. The alkoxy groups include, but are not limited to, methoxy, ethoxy, propoxy, butoxy, and other alkoxy groups each having about 1 to 6 carbon atoms. The N-substituted amino groups include, for example, N,N-dimethylamino, N,N-diethylamino, and piperidino groups.

Preferred $R^c$, $R^d$, and $R^e$ include, for example, hydrogen atom, hydrocarbon groups [e.g., $C_1$–$C_6$ aliphatic hydrocarbon groups (particularly $C_1$–$C_4$ aliphatic hydrocarbon groups), $C_6$–$C_{14}$ aryl groups (e.g., phenyl group), cycloalkyl groups (e.g., cycloalkyl groups each having about 3 to 8 members), haloalkyl groups (e.g., trifluoromethyl group, and other $C_1$–$C_6$ haloalkyl group, particularly $C_1$–$C_4$ haloalkyl groups)], heterocyclic groups, substituted oxycarbonyl groups (e.g., $C_1$–$C_6$ alkoxy-carbonyl groups, aryloxycarbonyl groups, aralkyloxycarbonyl groups, and cycloalkyloxycarbonyl groups), carboxyl group, substituted or unsubstituted carbamoyl groups, cyano group, nitro group, sulfur acid groups, sulfur acid ester groups, and acyl groups. Typically preferred $R^c$ and $R^d$ are, for example, hydrogen atom, $C_1$–$C_6$ aliphatic hydrocarbon groups (particularly $C_1$–$C_4$ aliphatic hydrocarbon groups), $C_6$–$C_{14}$ aryl groups (e.g., phenyl group), cycloalkyl groups (e.g., cycloalkyl groups each having about 3 to 8 members), haloalkyl groups (e.g., trifluoromethyl group, and other $C_1$–$C_6$ haloalkyl groups, particularly $C_1$–$C_4$ haloalkyl groups), substituted oxycarbonyl groups (e.g., $C_1$–$C_6$ alkoxy-carbonyl groups, aryloxycarbonyl groups, aralkyloxycarbonyl groups, and cycloalkyloxycarbonyl groups), and cyano group. Typically preferred $R^e$ includes, for example, hydrogen atom, and $C_1$–$C_6$ aliphatic hydrocarbon groups (especially, $C_1$–$C_4$ aliphatic hydrocarbon groups).

The rings formed by $R^c$, $R^d$, and $R^e$ ($R^c$ and $R^d$, $R^c$ and $R^e$, $R^d$ and $R^e$, or $R^c$ and $R^d$ and $R^e$) together with the adjacent carbon atom or carbon—carbon bond include cyclopropane, cyclobutane, cyclopentane, cyclopentene, cyclohexane, cyclohexene, cyclooctane, cyclododecane, and other alicyclic carbon rings (e.g., cycloalkane rings and cycloalkene rings) each having about 3 to 20 members. These rings may have a substituent, and to these rings, another ring (a non-aromatic ring or an aromatic ring) may be condensed.

Illustrative electron attracting groups Y include, but are not limited to, methoxycarbonyl, ethoxycarbonyl, and other alkoxycarbonyl groups; phenoxycarbonyl, and other aryloxycarbonyl groups; formyl, acetyl, propionyl, benzoyl, and other acyl groups; cyano group; carboxyl group; carbamoyl, N,N-dimethylcarbamoyl, and other substituted or unsubstituted carbamoyl groups; —CH=N—R, where R is, for example, an alkyl group; phenyl, naphthyl, and other aryl groups; vinyl, 1-propenyl, ethynyl, and other 1-alkenyl groups or 1-alkynyl groups.

The rings which may be formed by Y and at least one of $R^c$, $R^d$, and $R^e$ with the adjacent carbon atom or carbon—carbon bond include, but are not limited to, cyclopentadiene ring, pyrrole ring, furan ring, and thiophene ring.

Typical active olefins of the formula (3) include the compounds exemplified as the active unsaturated compounds (B1–1).

[Reaction]

A reaction between the alcohol of the formula (2) and the active olefin of the formula (3) can be performed in accordance with the procedure described in the reaction between the compound (A) and the compound (B).

In this reaction, a 1,3-dihydroxy compound of the formula (4) is supposed to be formed in the following manner. A 1-hydroxyalkyl radical which is formed in a system and corresponds to the alcohol of the formula (2) attacks and is added to a carbon atom at the β-position of the group Y of the two carbon atoms constituting an unsaturated bond of the active olefin of the formula (3), and oxygen attacks a radical at the α-position formed through addition to yield a 1,3-dihydroxy compound of the formula (4).

In the compound of the formula (4) formed through the reaction, when Y is an alkoxycarbonyl group, aryl oxycarbonyl group, or another ester group, or a carboxyl group, a cyclization reaction may further proceed in the system to yield a furanone derivative (α-hydroxy-γ-butyrolactone derivative) of the formula (6), as described later. The yield of the furanone derivative can be improved by controlling the type and proportion of the co-catalyst or further subjecting the product to aging after the addition reaction (or further oxidation reaction). A reaction temperature in the aging period is set higher than that in the addition reaction in many cases. The furanone derivative can be also produced by isolating the compound of the formula (4), for example dissolving the compound in a solvent, and heating the solution according to necessity. Such solvents include, but are not limited to, the solvents mentioned later, and benzene, toluene, and other aromatic hydrocarbons; cyclohexane, and other alicyclic hydrocarbons; acetone, cyclohexanone, and other ketones; diethyl ether, tetrahydrofuran, and other ethers; methanol, ethanol, isopropanol, and other alcohols. A reaction temperature in this procedure is, for example, about 0° C. to 150° C., and preferably about 30° C. to 100° C.

2. Production of α-Hydroxy-γ-butyrolactone Derivative

According to the invented process for producing an α-hydroxy-γ-butyrolactone derivative, the alcohol of the formula (2) is allowed to react with the α,β-unsaturated carboxylic acid derivative of the formula (5) in the presence of molecular oxygen by catalysis of the imide compound of the formula (1) to yield the α-hydroxy-γ-butyrolactone derivative of the formula (6).

[Alcohol]

The alcohols of the formula (2) include similar alcohols to those in the production of the 1,3-dihydroxy compound.

[α,β-Unsaturated Carboxylic Acid Derivative]

The substituents $R^c$, $R^d$, and $R^e$ in the formula (5) are similar to $R^c$, $R^d$, and $R^e$ in the formula (3). Organic groups in $R^f$ include organic groups that do not adversely affect the reaction (e.g., organic groups which are not reactive in reaction conditions according to the invented process) such as hydrocarbon groups and heterocyclic groups. If the compound of the formula (5) has a substituted oxycarbonyl group in addition to —$CO_2R^f$ group indicated in the formula (5), the —$CO_2R^f$ group is involved in a cyclization reaction, but the other substituted oxycarbonyl group can remain as intact in the product. The other substituted oxycarbonyl group is therefore included in the non-reactive organic groups.

When at least one of $R^c$ and $R^d$ is a haloalkyl group, a substituted oxycarbonyl group, a carboxyl group, a substituted or unsubstituted carbamoyl group, a cyano group, a nitro group, a sulfur acid group, a sulfur acid ester group, and another electron attracting organic group, a target α-hydroxy-γ-butyrolactone derivative can be obtained in a particularly high yield.

The substituent $R^f$ is often a hydrogen atom or a hydrocarbon group, and is preferably a $C_1$–$C_6$ alkyl group (especially a $C_1$–$C_4$ alkyl group), a $C_2$–$C_6$ alkenyl group (especially a $C_2$–$C_4$ alkenyl group), or a $C_6$–$C_{10}$ aryl group, for example.

Typical examples of the α,β-unsaturated carboxylic acid derivatives of the formula (5) include, but are not limited to, (meth)acrylic acid; methyl (meth)acrylate, ethyl (meth)acrylate, isopropyl (meth)acrylate, phenyl (meth)acrylate, and other (meth)acrylic esters; crotonic acid; methyl crotonate, ethyl crotonate, and other crotonic esters; 3-methyl-2-butenoic acid; methyl 3-methyl-2-butenoate, ethyl 3-methyl-2-butenoate, and other 3-methyl-2-butenoic esters; 2-pentenoic acid; methyl 2-pentenoate, ethyl 2-pentenoate, and other 2-pentenoic esters; 2-octenoic acid; methyl 2-octenoate, ethyl 2-octenoate, and other 2-octenoic esters; cinnamic acid; methyl cinnamate, ethyl cinnamate, and other cinnamic esters; 4,4,4-trifluoro-2-butenoic acid; methyl 4,4,4-trifluoro-2-butenoate, ethyl 4,4,4-trifluoro-2-butenoate, and other 4,4,4-trifluoro-2-butenoic esters; maleic acid; dimethyl maleate, diethyl maleate, and other maleic esters; fumaric acid; dimethyl fumarate, diethyl fumarate, and other fumaric esters; 3-cyanoacrylic acid; methyl 3-cyanoacrylate, ethyl 3-cyanoacrylate, and other 3-cyanoacrylic esters, and other α,β-unsaturated carboxylic acids each having about 2 to 15 carbon atoms or esters thereof (e.g., $C_1$–$C_6$ alkyl esters, $C_2$–$C_6$ alkenyl esters, and aryl esters).

[Reaction]

The proportion of the alcohol of the formula (2) to the α,β-unsaturated carboxylic acid ester of the formula (5) can be appropriately selected with reference to the types (costs, reactivity) and combination of the both compounds. For example, the alcohol may be used in excess amounts (e.g., about 2 to 50 times by mole) to the α,β-unsaturated carboxylic acid derivative, or vice versa, the α,β-unsaturated carboxylic acid derivative may be used in excess amounts to the alcohol.

According to the invented process, the reaction can smoothly proceed even under relatively mild conditions. A reaction temperature can be appropriately selected according to the types of the alcohol compound and the α,β-unsaturated carboxylic acid derivative, and is, for example, about 0° C. to 150° C., and preferably about 30° C. to 100° C. The reaction can be carried out at atmospheric pressure or under a pressure (under a load). When the reaction is conducted under a pressure, the pressure is usually about 1 to 100 atm (e.g. 1.5 to 80 atm), and preferably about 2 to 70 atm. A reaction time can be appropriately selected within a range of, for example, 30 minutes to 48 hours, depending on the reaction temperature and pressure.

The reaction can be performed in a batch system, a semi-batch system, a continuous system, and other conventional manners in the presence of, or under flow of, molecular oxygen.

According to the invented process, an α,β-dihydroxycarboxylic acid derivative (a kind of the compounds of the formula (4)) shown by the following formula (21) is formed as a reaction intermediate:

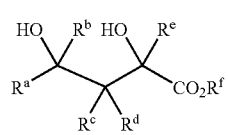

(21)

wherein $R^a$, $R^b$, $R^c$, $R^d$, $R^e$, and $R^f$ have the same meanings as defined above. This compound is supposed to be formed in the following manner. A 1-hydroxyalkyl radical which is formed in the system and corresponds to the alcohol of the formula (2) attacks and is added to the β-position of the α,β-unsaturated carboxylic acid derivative of the formula (5), and oxygen attacks a radical at the α-position formed through addition to yield the compound in question. The formed α,β-dihydroxycarboxylic acid derivative of the formula (21) undergoes cyclization under reaction conditions to yield the target α-hydroxy-γ-butyrolactone derivative of the formula (6).

When a primary alcohol is used as the alcohol of the formula (2) (i.e., $R^a$ is a hydrogen atom), a β-acyl-α-hydroxycarboxylic acid derivative of the following formula (22) may be formed, in addition to the compound of the formula (6). This is probably because an acyl radical ($R^bCO.$) is formed in the system.

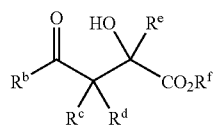

(22)

wherein $R^b$, $R^c$, $R^d$, $R^e$, and $R^f$ have the same meanings as defined above.

After the completion of the reaction, reaction products can be easily separated and purified in a conventional technique, such as filtration, concentration, distillation, extraction, crystallization, recrystallization, column chromatography and other separation means, or any combination of these separation means.

The α-hydroxy-γ-butyrolactone derivative can be also produced by isolating the α,β-dihydroxycarboxylic acid derivative of the formula (21), and, for example, dissolving the compound in a solvent, and heating the solution according to necessity, as described above.

[α-Hydroxy-γ-butyrolactone Derivative 1]

The invented α-hydroxy-γ-butyrolactone derivative of the formula (6b) can be produced by using a corresponding alicyclic alcohol, i.e., an alcohol in which $R^a$ and $R^b$ are combined to form a non-aromatic carbon ring with the adjacent carbon atom as a material alcohol in the aforementioned process for producing an α-hydroxy-γ-butyrolactone derivative.

The ring A in the formula (6b) is a non-aromatic carbon ring. Such non-aromatic carbon rings include, but are not limited to, cyclopropane, cyclobutane, cyclopentane, cyclopentene, cyclohexane, cyclohexene, cyclooctane, cyclodecane, cyclododecane, adamantane, and other non-aromatic carbon rings (e.g., cycloalkane rings, cycloalkene rings, and bridged rings) each having about 3 to 20 members (preferably about 3 to 15 members, more preferably about 5 to 15 members, and typically about 5 to 8 members). These rings may have substituents, and to these rings, another ring (a non-aromatic ring or an aromatic ring) may be condensed. Such substituents include halogen atoms, methyl group and other $C_1$–$C_4$ alkyl groups, hydroxyl group, methoxy group and other $C_1$–$C_4$ alkoxy groups, and oxo groups. The organic groups in $R^c$, $R^d$, and $R^e$, and preferred $R^c$, $R^d$, and $R^e$ are similar to those stated above.

Illustrative compounds of the formula (6b) include, for example, 3-hydroxy-2-oxo-1-oxaspiro[4.4]nonane, 3-hydroxy-3-methyl-2-oxo-1-oxaspiro[4.4]nonane, 4-ethoxycarbonyl-3-hydroxy-2-oxo-1-oxaspiro[4.4]nonane, 3-hydroxy-2-oxo-1-oxaspiro[4.5]decane, 3-hydroxy-3-methyl-2-oxo-1-oxaspiro[4.5]decane, 4-ethoxycarbonyl-3-hydroxy-2-oxo-1-oxaspiro[4.5]decane, and 3-hydroxy-2-oxo-1-oxaspiro[4.7]dodecane.

The compounds of the formula (6b) can be used as materials for pharmaceuticals, agricultural chemicals, and other fine chemicals. For example, when a compound having a hydrogen atom at the β-position is converted into an ester of a carboxylic acid (e.g., (meth)acrylic acid or a dicarboxylic acid), the ester itself is insoluble in alkalis but is easily decomposed by acids to yield an alkali-soluble carboxylic acid (a lactone ring is eliminated as an α,β-unsaturated lactone). The lactone ring is hydrophilic. Accordingly, these compounds are useful as monomers or materials thereof for resist resins (e.g., acrylic resins, and polyesters) which have satisfactory eliminating property and adhesion to a substrate.

[α-Hydroxy-γ-butyrolactone Derivative 2]

The invented α-hydroxy-γ-butyrolactone derivative of the formula (6c) can be produced by using an alcohol where $R^a$ and $R^b$ are each a hydrogen atom, a hydrocarbon group, or a heterocyclic group as the alcohol of the formula (2) and using a compound where $R^c$ is a haloalkyl group, a substituted oxycarbonyl group, a cyano group or an aryl group as the α,β-unsaturated carboxylic acid derivative of the formula (5) in the aforementioned process for producing an α-hydroxy-γ-butyrolactone derivative.

In the formula (6c), the hydrocarbon groups and heterocyclic groups indicated by $R^{a1}$ and $R^{b1}$, and preferred $R^{a1}$ and $R^{b1}$ are similar to those exemplified as the hydrocarbon groups and heterocyclic groups in $R^a$ and $R^b$, and as preferred groups $R^a$ and $R^b$. The organic groups in $R^d$ and $R^e$, and preferred $R^d$ and $R^e$ are similar to those stated above. The rings which may be formed by $R^{c1}$, $R^d$, and $R^e$ with the adjacent carbon atom or carbon—carbon single bond include the rings which may be formed by $R^c$, $R^d$, and $R^e$ with the adjacent carbon atom or carbon—carbon single bond.

In the α-hydroxy-γ-butyrolactone derivative 2, $R^{c1}$ is a haloalkyl group, a substituted oxycarbonyl group, a cyano group, or an aryl group. Practical examples of these groups include those stated above. Among them, preferred $R^{c1}$ includes trifluoromethyl group, and other $C_1$–$C_6$ haloalkyl groups (especially $C_1$–$C_4$ haloalkyl groups); methoxycarbonyl, ethoxycarbonyl, isopropoxycarbonyl, and other $C_1$–$C_6$ alkoxy-carbonyl groups (especially $C_1$–$C_4$ alkoxy-carbonyl groups); phenyloxycarbonyl group, and other $C_6$–$C_{10}$ aryloxy-carbonyl groups; benzyloxycarbonyl group, and other $C_7$–$C_{11}$ aralkyloxycarbonyl groups; cyclohexyloxycarbonyl group, and other $C_5$–$C_6$ cycloalkyloxy-carbonyl groups; cyano group; and phenyl group, and other $C_6$–$C_{10}$ aryl groups.

Typical examples of the compounds of the formula (6c) include β-trifluoromethyl-α-hydroxy-γ,γ-dimethyl-γ-butyrolactone, α-hydroxy-β-methoxycarbonyl-γ,γ-dimethyl-γ-butyrolactone, α-hydroxy-β-methoxycarbonyl-γ-methyl-γ-butyrolactone, α-hydroxy-β-methoxycarbonyl-α,γ,γ,-trimethyl-γ-butyrolactone, β-ethoxycarbonyl-α-hydroxy-γ,γ-dimethyl-γ-butyrolactone, β-ethoxycarbonyl-α-hydroxy-γ-methyl-γ-butyrolactone, β-ethoxycarbonyl-α-hydroxy-α,γ,γ-trimethyl-γ-butyrolactone, β-cyano-α-hydroxy-γ,γ-dimethyl-γ-butyrolactone, and α-hydroxy-γ,γ-dimethyl-β-phenyl-γ-butyrolactone.

The α-hydroxy-γ-butyrolactone derivatives 2 are useful as materials for pharmaceuticals, agricultural chemicals, and other fine chemicals.

Of the derivatives, for example, when a compound where $R^d$ is a hydrogen atom is converted into an ester of a carboxylic acid (e.g., (meth)acrylic acid, or a dicarboxylic acid), the ester itself is insoluble in alkalis but is easily decomposed by acids to yield an alkali-soluble carboxylic acid. This is because the ester has an electron attracting group such as a haloalkyl group, a substituted oxycarbonyl group, a cyano group or an aryl group at the α-position of a carbon atom to which the ester group is bonded, and the hydrogen atom is very easily withdrawn or eliminated. Accordingly, this compound is useful as a monomer or its material for resist resins (e.g., acrylic resins, and polyesters) which have satisfactory eliminating property and adhesion to a substrate. Especially, compounds where $R^c$ is a substituted oxycarbonyl group or a cyano group are highly hydrophilic and serve to improve the adhesion to a substrate.

[α-Hydroxy-γ-butyrolactone Derivative 3]

The invented α-hydroxy-γ-butyrolactone derivative of the formula (6d) can be produced by using an alcohol where $R^a$ is a hydrogen atom and $R^b$ is a hydrocarbon group or a heterocyclic group as the material alcohol of the formula (2) in the aforementioned process for producing an α-hydroxy-γ-butyrolactone derivative.

In the formula (6d), the hydrocarbon groups and heterocyclic groups indicated by $R^{b2}$, and preferred $R^{b2}$ are similar to the groups exemplified as the hydrocarbon groups and heterocyclic groups in $R^b$, and as preferred $R^b$. The organic groups in $R^d$ and $R^e$, and preferred $R^d$ and $R^e$ are similar to those stated above.

Typical examples of the compounds of the formula (6d) are α-hydroxy-γ-methyl-γ-butyrolactone, α-hydroxy-α,γ-dimethyl-γ-butyrolactone, γ-ethyl-α-hydroxy-γ-butyrolactone, α-hydroxy-γ-propyl-γ-butyrolactone, γ-butyl-α-hydroxy-γ-butyrolactone, α-hydroxy-γ-pentyl-γ-butyrolactone, γ-hexyl-α-hydroxy-γ-butyrolactone, and α-hydroxy-γ-phenyl-γ-butyrolactone.

The α-hydroxy-γ-butyrolactone derivatives 3 can be used as materials for pharmaceuticals, agricultural chemicals, and other fine chemicals. Of the derivatives, compounds where $R^d$ is a hydrogen atom can be used as monomers materials thereof for resist resins (e.g., acrylic resins and polyesters) having satisfactory eliminating property and adhesion to a substrate, for the same reason as mentioned above.

[α-(Meth)acryloyloxy-γ-butyrolactone Derivative]

In the invented α-(meth)acryloyloxy-γ-butyrolactone derivative of the formula (8), hydrocarbon groups and heterocyclic groups indicated by $R^{a3}$ and $R^{b3}$, and preferred $R^{a3}$ and $R^{b3}$ are similar to the groups exemplified as the hydrocarbon groups and heterocyclic groups in $R^a$ and $R^b$, and as preferred $R^a$ and $R^b$. The organic groups in $R^c$, $R^d$ and $R^e$, and preferred $R^c$, $R^d$ and $R^e$ are similar to those stated above.

Typical examples of the α-(meth)acryloyloxy-γ-butyrolactone derivatives of the formula (8) include, but are not limited to, acrylic esters and methacrylic esters corresponding to the compounds exemplified as typical examples of the compounds of the formula (6b), (6c), and (6d), as well as acrylic esters and methacrylic esters corresponding to α-hydroxy-γ,γ-dimethyl-γ-butyrolactone, α-hydroxy-α,γ,γ-trimethyl-γ-butyrolactone, α-hydroxy-β,γ,γ-trimethyl-γ-butyrolactone, γ-hexyl-α-hydroxy-γ-methyl-γ-butyrolactone, and γ-t-butyl-α-hydroxy-γ-methyl-γ-butyrolactone.

The α-(meth)acryloyloxy-γ-butyrolactone derivatives of the formula (8) can be produced, for example, by the following process (i), (ii) or (iii). In the process (i), an α-hydroxy-γ-butyrolactone derivative (hereinafter referred to as "α-hydroxy-γ-butyrolactone derivative 4") is allowed to react with (meth)acrylic acid in the presence of an acid catalyst such as hydrochloric acid, sulfuric acid, or p-toluenesulfonic acid. The α-hydroxy-γ-butyrolactone derivative 4 is obtained by using an alcohol where each of $R^a$ and $R^b$ is a hydrogen atom, a hydrocarbon group or a heterocyclic group as the material alcohol of the formula (2) in the invented process for producing an α-hydroxy-γ-butyrolactone derivative. In the process (ii), the α-hydroxy-γ-butyrolactone derivative 4 is allowed to react with a (meth)acrylic acid halide in the presence of a base such as triethylamine. In the process (iii), the α-hydroxy-γ-butyrolactone derivative 4 and a (meth) acrylic ester is subjected to transesterification in the presence of a transesterification catalyst. In the processes (i) and (ii), the reaction can be performed under usual esterification conditions. In the process (iii), the transesterification can be performed using a conventional transesterification catalyst such as sodium alkoxides, aluminium alkoxides, and titanates. However, the compounds of the formula (8) can be obtained in high yields by using vinyl (meth) acrylate, propenyl (meth)acrylate, and another (meth)acrylic acid $C_2$–$C_4$ alkenyl ester as the (meth)acrylic ester and by using a compound of Group 3 element of the Periodic Table of Elements (e.g., samarium iodide, samarium triflate, samarium complexes, and other samarium compounds) as the transesterification catalyst.

The α-(meth)acryloyloxy-γ-butyrolactone derivatives of the formula (8), particularly compounds where $R^d$ is a hydrogen atom themselves are insoluble in alkalis but are easily decomposed by acids to yield alkali-soluble carboxylic acids. In addition, the lactone ring is highly hydrophilic. Accordingly, polymers including such compounds as monomeric components have satisfactory eliminating property and are highly adhesive to a substrate, and can be advantageously used as resist materials.

[Polymer and Photosensitive Resinous Composition]

In the invented polymers each having a structural unit of the formula (9), the substituents $R^{a3}$, $R^{b3}$, $R^c$, $R^d$, $R^e$, and $R^g$ are similar to those in the α-(meth)acryloyloxy-γ-butyrolactone derivatives of the formula (8).

The polymer having a structural unit of the formula (9) may be a homopolymer of the α-(meth)acryloyloxy-γ-butyrolactone derivative of the formula (8) or a copolymer of the α-(meth)acryloyloxy-γ-butyrolactone derivative of the formula (8) with another copolymerizable monomer. Such copolymerizable monomers include, but are not limited to, unsaturated carboxylic acids [e.g., (meth)acrylic acid, fumaric acid, maleic acid, and itaconic acid], esters of the unsaturated carboxylic acids [esters of the unsaturated carboxylic acids with aliphatic, alicyclic or aromatic alcohols which may have a substituent, phenols, or hydroxylactones], (meth)acrylonitrile, and styrenic monomers. Preferred copolymerizable monomers are 1-(1-(meth)acryloyloxy-1-methylethyl)adamantane, 3-(1-(meth)acryloyloxy-1-methylethyl)-1-adamantanol, 3-((meth)acryloyloxy)-1-adamantanol, and other (meth)acrylic ester compounds each having an adamantane skeleton having one or more hydroxyl groups, which may be protected by a protective group, on the adamantane ring; 2-hydroxy-6-((meth)acryloyloxy)-tricyclo[5.2.1.0$^{2,6}$]decane, 2-hydroxy-6-((meth) acryloyloxy)tricyclo[5.2.1.0$^{2,6}$]decane, 2-(1-(meth)acryloyloxy-1-methylethyl)-tricyclo[5.2.1.0$^{2,6}$]decane, 6-hydroxy-2-(1-(meth)acryloyloxy-1-methylethyl)-tricyclo[5.2.1.0$^{2,6}$] decane, and other (meth)acrylic ester compounds having an alicyclic carbon ring. These monomers can impart etching resistance to the resulting polymer. The ratio of the α-(meth) acryloyloxy-γ-butyrolactone derivative of the formula (8) to the other monomer (e.g., the (meth) acrylic ester compound having an alicyclic carbon ring) in the copolymer is not particularly limited, and the former/the latter is, for example, about 25/75 to 70/30.

The polymer has a weight average molecular weight of, for example, about 5000 to 50000, and preferably about 7000 to 20000.

The polymer can be produced by a conventional polymerization process. In this procedure, each one or more species of the α-(meth)acryloyloxy-γ-butyrolactone derivatives of the formula (8) and the copolymerizable monomers can be respectively employed.

The polymer has a lactone ring and is highly hydrophilic, and has a high adhesion to a substrate when used as a resist resin. The polymer has an ester group bonded to the α-position of a carbonyl group of the lactone ring and is easily decomposed by acids to eliminate the lactone ring. The polymer is therefore useful as a photoresist resin having satisfactory definition (photosensitivity, sensitivity) and adhesion to a substrate.

The invented photosensitive resinous composition (e.g., a photoresist resinous composition) is characterized by including the polymer having a structural unit of the formula (9) and a light-activatable acid generator.

Such light-activatable acid generators include conventional compounds that efficiently generate acids by exposure to light. Such compounds include, but are not limited to, diazonium salts, iodonium salts (e.g., diphenyliodo hexafluorophosphate), sulfonium salts (e.g., triphenylsulfonium hexafluoroantimonate, triphenylsulfonium hexafluorophosphate, and triphenylsulfonium methanesulfonate), sulfonates [e.g., 1-phenyl-1-(4-methylphenyl)sulfonyloxy-1-benzoylmethane, 1,2,3-trisulfonyloxymethylbenzene, 1,3-dinitro-2-(4-phenylsulfonyloxymethyl)benzene, and 1-phenyl-1-(4-methylphenylsulfonyloxymethyl)-1-hydroxy-1-benzoylmethane], oxathiazole derivatives, s-triazine derivatives, disulfone derivatives (e.g., diphenyldisulfone), imide compounds, oxime sulfonates, diazonaphthoquinone, and benzoin tosylate. Each of these light-activatable acid generators can be used alone or in combination.

The proportion of the light-activatable acid generator can be appropriately selected according to the strength of an acid formed by light irradiation or the content of the structural unit of the formula (9) in the polymer, and is, for example, about 0.1 to 30 parts by weight, preferably about 1 to 25 parts by weight, and more preferably about 2 to 20 parts by weight relative to 100 parts by weight of the polymer.

The photosensitive resinous composition may further comprise, for example, alkali-soluble resins (e.g., novolak resins, phenol resins, imide resins, and carboxyl-group-containing resins), and other alkali-soluble components, coloring agents (e.g., dyes), and organic solvents (e.g., hydrocarbons, halogenated hydrocarbons, alcohols, esters, ketones, ethers, Cellosolves, Carbitols, glycol ether esters, and mixtures of these solvents).

The invented photosensitive resinous composition can be prepared by mixing the polymer (acid sensitive polymer) and the light-activatable acid generator, and the organic solvent or the like according to necessity, and removing, where necessary, contaminants by a filter or other conventional solid separation means.

Fine patterns can be precisely formed by applying the photosensitive resinous composition onto a base or a substrate, drying the applied composition, irradiating the applied film (resist film) with a light beam through a predetermined mask (or further subjecting the film to post exposure baking) to form a patterned latent image, and subjecting the film to developing.

Such bases or substrates include, but are not limited to, silicon wafers, metals, plastics, glasses, and ceramics. The photoresist resinous composition can be applied by a conventional applying means such as spin coating device, dip coating device, and coating device by roller. The thickness of the coated film is, for example, about 0.1 to 20 μm and preferably about 0.3 to 2 μm.

Light beams having different wavelengths such as ultraviolet rays and X-rays can be employed for light exposure. For semiconductor resists, g-ray, 1-ray, and excimer lasers (e.g., XeCl, KrF, KrCl, ArF, and ArCl) can be employed. The irradiation energy is, for example, about 1 to 1000 mJ/cm², and preferably about 10 to 500 mJ/cm².

Light irradiation allows the light-activatable acid generator to form an acid, and this acid permits the cyclic moiety of the structural unit of the formula (9) of the polymer to rapidly eliminate. Thus, a carboxyl group is formed and is involved in solubilization. Accordingly, a predetermined pattern can be precisely formed by developing the film with water or an alkali developer.

The invented resinous compositions can be used for various applications such as circuit forming materials (e.g., resists for semiconductor production, printed wiring boards), and image-forming materials (e.g., printing plate materials, and relief printing materials).

[Production of β-Hydroxy-γ-butyrolactone Derivative]

According to the invented process for producing a β-hydroxy-γ-butyrolactone derivative, a compound where $R^d$ is a hydrogen atom in the α-hydroxy-γ-butyrolactone derivative of the formula (6), i.e., the compound of the formula (6a) is dissolved in a solvent.

Such solvents include, but are not limited to, the aforementioned solvents. A reaction rate can be enhanced by adding a small portion of water, or a catalytic amount of an acid to a reaction system. Such acids include, for example, sulfuric acid, hydrochloric acid, nitric acid, phosphoric acid, p-toluenesulfonic acid, a heteropolyacid, or a cation exchange resin.

A reaction temperature is, for example, about 0° C. to 150° C., and preferably about 20° C. to 100° C. The reaction can smoothly proceed even at a temperature ranging from room temperature to about 40° C.

In a reaction mixture, an α,β-unsaturated-γ-butyrolactone derivative of the following formula (23):

(23)

wherein $R^a$, $R^b$, $R^c$, and $R^e$ have the same meanings as defined above, is observed. Accordingly, the isomerization reaction is supposed to proceed in the following manner. In the reaction, the α-hydroxy-γ-butyrolactone derivative of the formula (6a) undergoes dehydration reaction to yield the α,β-unsaturated-γ-butyrolactone derivative of the formula (23), and this compound is then hydrated.

After the completion of the reaction, reaction products can be easily separated and purified in a conventional technique, such as filtration, concentration, distillation, extraction, crystallization, recrystallization, column chromatography and other separation means, or any combination of these separation means.

[γ-Butyrolactone Derivative]

In the invented γ-butyrolactone derivatives of the formula (10), $R^a$, $R^c$, $R^d$, and $R^e$ have the same meanings as in the formulae (2) and (5). Preferred $R^a$ includes, for example, hydrogen atom; methyl, ethyl, propyl, isopropyl, butyl, isobutyl, s-butyl, t-butyl, pentyl, hexyl, octyl, decyl, and other $C_1$–$C_{10}$ aliphatic hydrocarbon groups (especially, alkyl groups); cyclopentyl, cyclohexyl, cyclohexenyl, and other $C_3$–$C_{15}$ cycloalkyl groups or cycloalkenyl groups. More preferred $R^a$ includes, for example, hydrogen atom; methyl, ethyl, propyl, isopropyl, butyl, isobutyl, s-butyl, and other $C_1$–$C_4$ alkyl groups. Preferred $R^c$, $R^d$, and $R^e$ are the same as in the formula (5).

The bridged cyclic hydrocarbon group in $R^{b4}$ in the formula (10) includes, for example, bicyclic, tricyclic or tetracyclic bridged hydrocarbon groups, of which bicyclic or tricyclic bridged hydrocarbon groups are preferred.

Illustrative bridged rings in the bridged cyclic hydrocarbon groups include the bridged rings exemplified in the explanation of the formula (2) The bridged cyclic hydrocarbon group may be bonded to the γ-butyrolactone ring through any carbon atom constituting the bridged ring, but should be preferably bonded through a carbon atom at a bridgehead position (junction position).

These bridged rings may have a variety of substituents. Such substituents include, but are not limited to, halogen atoms (fluorine, chlorine, bromine, and iodine atoms), oxo group, hydroxyl groups which may be protected by a protective group, hydroxymethyl groups which may be protected by a protective group, amino groups which may be protected by a protective group, carboxyl groups which may be protected by a protective group, substituted oxycarbonyl groups, substituted or unsubstituted carbamoyl groups, nitro group, acyl groups, cyano group, alkyl groups (e.g., methyl, ethyl, and other $C_1$–$C_4$ alkyl groups), cycloalkyl groups, aryl groups (e.g., phenyl, and naphthyl groups), and heterocyclic groups. Especially, compounds having hydrophilic substituents are useful as intermediate materials for monomers of resist resins. Such hydrophilic substituents include, for example, oxo group, hydroxyl groups which may be protected by a protective group, hydroxymethyl groups which may be protected by a protective group, amino groups which may be protected by a protective group, and carboxyl groups which may be protected by a protective group. These compounds have satisfactory adhesion to a substrate.

As the protective groups for hydroxyl group and hydroxymethyl group, protective groups for amino group, and protective groups for carboxyl group, the conventional protective groups mentioned above can be employed.

Illustrative compounds of the formula (10) include, for example, γ-(1-adamantyl)-α-hydroxy-γ-butyrolactone, γ-(1-adamantyl)-α-hydroxy-γ-methyl-γ-butyrolactone, γ-(1-adamantyl)-γ-ethyl-α-hydroxy-γ-butyrolactone, γ-(1-adamantyl)-α-hydroxy-γ-isopropyl-γ-butyrolactone, γ-(1-adamantyl)-α-hydroxy-α,γ-dimethyl-γ-butyrolactone, γ-(1-adamantyl)-α-hydroxy-β,γ-dimethyl-γ-butyrolactone, γ-(3-hydroxyadamant-1-yl)-α-hydroxy-γ-methyl-γ-butyrolactone, γ-(3-carboxyadamant-1-yl)-α-hydroxy-γ-methyl-γ-butyrolactone, α-hydroxy-γ-methyl-γ-(3a-perhydroindenyl)-γ-butyrolactone, γ-(4a-decalinyl)-α-hydroxy-γ-methyl-γ-butyrolactone, γ-(8a-hydroxydecalin-4a-yl)-α-hydroxy-γ-methyl-γ-butyrolactone, α-hydroxy-γ-methyl-γ-(4a-perhydrofluorenyl)-γ-butyrolactone, α-hydroxy-γ-methyl-γ-(4a-perhydroanthracenyl)-γ-butyrolactone, α-hydroxy-γ-methyl-γ-(8a-perhydrophenanthrenyl)-γ-butyrolactone, α-hydroxy-γ-methyl-γ-(2-tricyclo[5.2.1.0$^{2,6}$]decanyl)-γ-butyrolactone, α-hydroxy-γ-(6-hydroxytricyclo[5.2.1.0$^{2,6}$]decan-2-yl)-γ-methyl-γ-butyrolactone, α-hydroxy-γ-methyl-γ-(2a-perhydroacenaphthenyl)-γ-butyrolactone, α-hydroxy-γ-methyl-γ-(3a-perhydrophenalenyl)-γ-butyrolactone, α-hydroxy-γ-methyl-γ-(1-norbornanyl)-γ-butyrolactone, and α-hydroxy-γ-methyl-γ-(2-norbornen-1-yl)-γ-butyrolactone; and acryloyl derivatives and methacryloyl derivatives corresponding to these compounds.

Of the γ-butyrolactone derivatives of the formula (10), a compound where R is a hydrogen atom (α-hydroxy-γ-butyrolactone derivative) can be produced by the invented process for producing an α-hydroxy-γ-butyrolactone derivative.

Specifically, the compound can be produced by allowing an alcohol of the following formula (24):

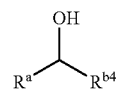

(24)

wherein $R^a$ and $R^{b4}$ have the same meanings as defined above, to react with the α,β-unsaturated carboxylic acid derivative of the formula (5) in the presence of molecular oxygen by catalysis of the imide compound of the formula (1).

Typical examples of the alcohols of the formula (24) include 1-adamantanemethanol, α-methyl-1-adamantanemethanol, α-ethyl-1-adamantanemethanol, α-isopropyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4a-decalinmethanol, 8a-hydroxy-α-methyl-4a-decalinmethanol, α-methyl-4a-perhydrofluorenemethanol, α-methyl-4a-perhydroanthracenemethanol, α-methyl-8a-perhydrophenanthrenemethanol, α-methyl-2-tricyclo[5.2.1.0$^{2,6}$]decanemethanol, 6-hydroxy-α-methyl-2-tricyclo[5.2.1.0$^{2,6}$]decanemethanol, α-methyl-2a-perhydroacenaphthenemethanol, α-methyl-3a-perhydrophenalenemethanol, α-methyl-1-norbornanemethanol, and α-methyl-2-norbornene-1-methanol.

The alcohol of the formula (24) can be obtained, for example, by reducing a carbonyl compound of the following formula (25):

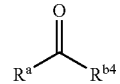

(25)

wherein $R^a$ and $R^{b4}$ have the same meanings as defined above, with, for example, lithium aluminium hydride, sodium borohydride or analogues thereof, and other metal hydrogen complex compounds or metal hydrogen compounds (hydrido reduction), or by subjecting the carbonyl compound of the formula (25) to catalytic reduction with hydrogen in the presence of a catalyst. Such catalysts include, for example, Ru—C, Cr—Cu, Rh—C, platinum oxide, and Raney nickel. The reduction can be performed in a solvent at a temperature of about −100° C. to 150° C. depending on the type of the reduction process. Such solvents include, but are not limited to, diethyl ether, tetrahydrofuran, and other ethers; hexane, and other aliphatic hydrocarbons; toluene, and other aromatic hydrocarbons; methanol, and other alcohols; methylene chloride, and other halogenated hydrocarbons; and acetic acid, and other carboxylic acids.

The carbonyl compound of the formula (25) can be prepared, for example, by allowing a bridged cyclic hydrocarbon of the following formula (26):

wherein $R^{b4}$ has the same meaning as defined above, to react with a 1,2-dicarbonyl compound of the following formula (27):

wherein $R^a$ has the same meaning as defined above, in the presence of oxygen, and a metallic compound and/or the imide compound of the formula (1).

Typical examples of the 1,2-dicarbonyl compound include biacetyl(2,3-butanedione), and 3,4-hexanedione. Molecular oxygen is often used as the oxygen. The metallic compound includes, but is not limited to, cobalt acetate, acetylacetonatocobalt, and other cobalt compounds, acetylacetonatovanadium, vanadyl acetylacetonato, and other vanadium compounds. The imide compound includes, for example, N-hydroxyphthalimide.

The proportion of the 1,2-dicarbonyl compound is, for example, about 1 to 50 moles, and preferably about 1.5 to 20 moles relative to 1 mole of the bridged cyclic hydrocarbon of the formula (26). The oxygen is used in excess amounts relative to the bridged cyclic hydrocarbon of the formula (26) in many cases. The proportion of the metallic compound is, for example, 0.00001 to 1 mole, and preferably about 0.0001 to 0.1 mole relative to 1 mole of the bridged cyclic hydrocarbon of the formula (26). The amount of the imide compound is, for example, about 0.00001 to 1 mole, and preferably about 0.001 to 0.7 mole relative to 1 mole of the bridged cyclic hydrocarbon of the formula (26). The metallic compound and the imide compound may be employed in combination. A reaction is generally performed in an organic solvent such as acetic acid, benzonitrile, or trifluoromethylbenzene. A reaction temperature is, for example, about 0° C. to 300° C., and preferably about 40° C. to 150° C. Reaction products can be separated and purified by filtration, concentration, distillation, crystallization, recrystallization, column chromatography, and other conventional separation means.

The compound of the formula (5) is the same as illustrated above. The reaction between the alcohol of the formula (24) and the compound of the formula (5) can be performed under the conditions described in the invented process for producing an α-hydroxy-γ-butyrolactone derivative.

[Production of α-(Meth)acryloyloxy-γ-butyrolactone Derivative]

Of the γ-butyrolactone derivatives of the formula (10), a compound where R is an acryloyl group or a methacryloyl group [α-(meth)acryloyloxy-γ-butyrolactone derivative] can be produced, for example, by the following process (i), (ii) or (iii). In the process (i), an α-hydroxy-γ-butyrolactone derivative where R is a hydrogen atom among the γ-butyrolactone derivatives of the formula (10) is allowed to react with (meth)acrylic acid in the presence of an acid catalyst such as hydrochloric acid, sulfuric acid, or p-toluenesulfonic acid. In the process (ii), the α-hydroxy-γ-butyrolactone derivative is allowed to react with a (meth) acrylic halide in the presence of a base such as triethylamine. In the process (iii), the α-hydroxy-γ-butyrolactone derivative is subjected to transesterification with a (meth)acrylic ester in the presence of a transesterification catalyst. In the processes (i) and (ii), the reaction can be performed under usual esterification conditions. In the process (iii), the transesterification can be performed using a conventional transesterification catalyst such as sodium alkoxides, aluminium alkoxides, and titanates. However, the α-(meth) acryloyloxy-γ-butyrolactone derivative can be obtained in a high yield by using vinyl (meth)acrylate, propenyl (meth)acrylate, and another (meth) acrylic acid $C_2$–$C_4$ alkenyl ester as the (meth)acrylic ester and by using a compound of Group 3 element of the Periodic Table of Elements (e.g., samarium iodide, samarium triflate, samarium complexes, and other samarium compounds) as the transesterification catalyst.

The invented γ-butyrolactone derivatives of the formula (10) are useful as materials for photosensitive resins, and other functional polymers, and materials for pharmaceuticals, agricultural chemicals, and other fine chemicals. Particularly, the α-(meth) acryloyloxy-γ-butyrolactone derivatives, especially compounds where $R^d$ is a hydrogen atom, are insoluble themselves in alkalis but are easily decomposed by acids to yield alkali-soluble carboxylic acids. In addition, a lactone ring is highly hydrophilic and the compounds are satisfactory in etching resistance due to the bridged ring bonded to the γ-position. Accordingly, polymers including such compounds as monomeric components have satisfactory eliminating property and are highly adhesive to a substrate, and can be advantageously used as resist resins.

For example, a photosensitive resinous composition (e.g., a photoresist resinous composition) can be prepared by mixing a homo- or co-polymer containing the α-(meth) acryloyloxy-γ-butyrolactone derivative as a monomer with the light-activatable acid generator.

3. Production of Conjugated Unsaturated Compound

The alcohol of the formula (2a) is allowed to react with the active olefin of the formula (3a) in the presence of molecular oxygen by catalysis of the imide compound of the formula (1) to yield the conjugated unsaturated compound of the formula (11).

Organic groups in $R^i$ and $R^j$ in the formula (2a) are the same as the organic groups in $R^a$ and $R^b$. Rings which are formed by $R^i$ and $R^j$ with the adjacent carbon atom include the rings which are formed by $R^a$ and $R^b$ with the adjacent carbon atom.

Preferred substituent $R^i$ includes, for example, hydrogen atom; methyl, ethyl, propyl, isopropyl, butyl, and other $C_1$–$C_4$ alkyl groups, and $C_6$–$C_{14}$ aryl groups. Preferred $R^j$ includes, for example, hydrogen atom, $C_1$–$C_{10}$ aliphatic hydrocarbon groups (e.g., methyl, ethyl, propyl, isopropyl, butyl, isobutyl, s-butyl, t-butyl, pentyl, hexyl, octyl, and decyl groups; particularly $C_1$–$C_{10}$ alkyl groups), and alicyclic hydrocarbon groups (e.g., cyclopentyl, cyclohexyl, cyclohexenyl, and other $C_3$–$C_{15}$ cycloalkyl groups or cycloalkenyl groups; and bridged cyclic hydrocarbon groups). Alternatively, $R^i$ and $R^j$ are preferably combined to form a non-aromatic carbon ring having about 3 to 15 members (particularly about 5 to 8 members) with the adjacent carbon atom.

The alcohols of the formula (2a) include a wide variety of primary alcohols. Typical examples of such alcohols include, but are not limited to, ethanol, 1-propanol, 1-butanol, 2-methyl-1-propanol, 1-pentanol, 1-hexanol, 1-octanol, 1-decanol, 1-hexadecanol, 2-buten-1-ol, and other saturated or unsaturated aliphatic primary alcohols each having about 2 to 30 (preferably about 2 to 20, and more preferably about 2 to 15) carbon atoms; cyclopentylmethyl alcohol, cyclohexylmethyl alcohol, 2-cyclohexylethyl alcohol, and other saturated or unsaturated alicyclic primary alcohols; 2-phenylethyl alcohol, 3-phenylpropyl alcohol, cinnamic alcohol, and other aromatic primary alcohols; and 2-(2-hydroxyethyl)pyridine, and other heterocyclic alcohols.

The compounds of the formula (3a) correspond to compounds where $R^c$ is a hydrogen atom among the compounds of the formula (3). The substituents $R^d$, $R^e$, and Y in the formula (3a) have the same meanings as in the formula (3).

A reaction can be performed in accordance with the invented process for producing a 1,3-dihydroxy compound. In this reaction, a compound corresponding to the formula (4) (a compound where $R^a = R^iR^jCH$ group, and $R^b = R^c = H$ in the formula (4)) can be formed in addition to the conjugated unsaturated compound of the formula (11). When a compound where $Y = CO_2R^f$ is used as the compound of the formula (3a), a compound corresponding to the formula (6) (a compound where $R^a = R^iR^jCH$ group, and $R^b = R^c = H$ in the formula (6)) can be formed in addition to the conjugated unsaturated compound of the formula (11).

For example, when n-propyl alcohol is allowed to react with ethyl acrylate, ethyl 2,4-dihydroxyhexanoate corresponding to the formula (4) and 4-ethyl-2-hydroxy-γ-butyrolactone corresponding to the formula (6) are formed under some conditions, in addition to the target ethyl sorbate.

The conjugated unsaturated compound of the formula (11) is supposed to be formed in the following manner. Initially, a dihydroxy compound corresponding to the formula (4) [a compound where $R^a = R^iR^jCH$ group, and $R^b = R^c = H$ in the formula (4)] is formed, and two molecules of water are then eliminated from this compound. Reaction products can be separated and purified in the same separation means as above.

4. Production of β-Hydroxyacetal Compound

The acetal of the formula (12) is allowed to react with the active olefin of the formula (3) in the presence of molecular oxygen by catalysis of the imide compound of the formula (1) to yield the β-hydroxyacetal compound of the formula (13).

In the formula (12), organic groups in $R^k$, $R^m$, and $R^n$ include organic groups similar to those in $R^a$ and $R^b$. Rings formed by $R^m$ and $R^n$ with the adjacent two oxygen atoms and carbon atom include, for example, 1,3-dioxolane ring and 1,3-dioxane ring. To these rings, substituents such as alkyl groups and halogen atoms can be bonded.

Preferred substituent $R^k$ includes, for example, hydrogen atom; methyl, ethyl, propyl, isopropyl, butyl, isobutyl, s-butyl, t-butyl, pentyl, hexyl, octyl, decyl, and other $C_1$–$C_{10}$ aliphatic hydrocarbon groups (especially, $C_1$–$C_4$ alkyl groups); cyclopentyl, cyclohexyl, cyclohexenyl, adamantyl, and other alicyclic hydrocarbon groups (cycloalkyl groups, cycloalkenyl groups, and bridged cyclic hydrocarbon groups) each having about 3 to 15 carbon atoms; and phenyl, naphthyl, and other $C_6$–$C_{14}$ aryl groups. Preferred $R^m$ and $R^n$ include, for example, hydrogen atom; methyl, ethyl, propyl, isopropyl, butyl, isobutyl, hexyl, and other $C_1$–$C_6$ aliphatic hydrocarbon groups (particularly, $C_1$–$C_4$ alkyl groups); and cyclopentyl, cyclohexyl, and other alicyclic hydrocarbon groups each having about 3 to 10 carbon atoms. Alternatively, $R^m$ and $R^n$ are preferably combined to form a ring with the adjacent two oxygen atoms and carbon atom.

The acetals of the formula (12) include compounds exemplified as the acetals (A1–3) each having a carbon-hydrogen bond at the adjacent position to an oxygen atom. Typical examples of such acetals include 1,3-dioxolane, 2-methyl-1,3-dioxolane, 2-ethyl-1,3-dioxolane, and other 1,3-dioxolane compounds; 2-methyl-1,3-dioxane, and other 1,3-dioxane compounds; and acetaldehyde dimethyl acetal, and other dialkyl acetals.

The active olefin of the formula (3) is the same as stated above. A reaction can be performed according to the invented process for producing an organic compound. Reaction products can be separated and purified in the same separation means as above.

In this reaction, the β-hydroxyacetal compound of the formula (13) is supposed to be formed in the following manner. Initially, a 1,1-di-substituted oxyalkyl radial corresponding to the acetal of the formula (12) is formed, and this radical attacks and is added to a carbon atom at the 1-position of the group Y between the two carbon atoms constituting an unsaturated bond of the active olefin of the formula (3), and oxygen attacks a radical at the α-position formed through addition.

5. Production of Hydroxy Compound

The compound of the formula (14) having a methine carbon atom is allowed to react with the active olefin of the formula (3) in the presence of molecular oxygen by catalysis of the imide compound of the formula (1) to yield at least one hydroxy compound selected from the formulae (15) and (16).

The organic groups in $R^o$, $R^p$ and $R^q$ in the formula (14) include organic groups similar to those in $R^a$ and $R^b$. Preferred organic groups include, for example, methyl, ethyl, propyl, isopropyl, butyl, isobutyl, s-butyl, t-butyl, pentyl, hexyl, octyl, decyl, and other $C_1$–$C_{10}$ aliphatic hydrocarbon groups (especially, $C_1$–$C_4$ alkyl groups); cyclopentyl, cyclohexyl, cyclohexenyl, adamantyl, and other alicyclic hydrocarbon groups (cycloalkyl groups, cycloalkenyl groups, and bridged cyclic hydrocarbon groups) each having about 3 to 15 carbon atoms; and phenyl, naphthyl, and other $C_6$–$C_{14}$ aryl groups.

The rings formed by $R^o$, $R^p$, and $R^q$ ($R^o$ and $R^p$, $R^p$ and $R^q$, $R^o$ and $R^q$, or $R^o$ and $R^p$ and $R^q$) together with the adjacent carbon atom include, but are not limited to, cyclopropane, cyclobutane, cyclopentane, cyclopentene, cyclohexane, cyclohexene, cyclooctane, cyclodecane, cyclododecane, and other monocyclic alicyclic carbon rings (cycloalkane rings and cycloalkene rings) each having about 3 to 20 members (preferably about 3 to 15 members, more preferably about 5 to 15 members, and typically about 5 to 8 members); adamantane ring, perhydroindene ring, decalin ring, perhydrofluorene ring, perhydroanthracene ring, perhydrophenanthrene ring, tricyclo[5.2.1.0$^{2,6}$]decane ring, perhydroacenaphthene ring, perhydrophenalene ring, norbornane ring, norbornene ring, and other bicyclic, tricyclic or tetracyclic bridged carbon rings. These rings may have substituents (e.g., groups similar to the substituents which the hydrocarbon groups in $R^a$ and $R^b$ may have).

When $R^o$, $R^p$, and $R^q$ are combined to form a bridged cyclic carbon ring with the adjacent carbon atom, the methine carbon atom indicated in the formula (14) should be preferably a carbon atom at a bridgehead position.

The compounds of the formula (14) having a methine carbon atom include, for example, compounds exemplified as the compounds (A3) such as the bridged cyclic compounds (A3–1a), the non-aromatic cyclic compounds (A3–1b) each having a hydrocarbon group bonded to its ring, and the chain compounds (A3–2) each having a methine carbon atom.

The active olefin of the formula (3) has the same meaning as above. A reaction can be performed according to the invented process for producing an organic compound. Reaction products can be separated and purified in the same separation means as above.

In this reaction, the hydroxy compound of the formula (15) or the hydroxy compound of the formula (16) is supposed to be formed in the following manner. A radical is formed at the methine carbon position of the compound of the formula (14), and the radical attacks and is added to a carbon atom at the α-position or a carbon atom at the β-position of the group Y between the two carbon atoms constituting an unsaturated bond of the active olefin of the formula (3), and oxygen attacks a radical at the α-position or β-position formed through addition to yield the hydroxy compound of the formula (15) or the hydroxy compound of the formula (16).

Of the hydroxy compounds of the formula (15) thus prepared, preferred compounds are compounds where $R^o$, $R^p$, and $R^q$ are combined to form a bridged cyclic carbon ring (e.g., adamantane ring) with the adjacent carbon atom, each of $R^c$, $R^d$, and $R^e$ is a hydrogen atom or a $C_1$–$C_4$ alkyl group, Y is an alkoxycarbonyl group (e.g., a $C_1$–$C_4$ alkoxy-carbonyl group), an aryloxycarbonyl group, an acyl group (e.g., a $C_1$–$C_4$ acyl group, or a benzoyl group) or a carboxyl group. Such compounds are useful as, for example, materials for pharmaceuticals, agricultural chemicals, and other fine chemicals, and materials for functional polymers.

6. Production of Carbonyl Compound

The compound of the formula (14) having a methine carbon atom is allowed to react with the active olefin of the formula (3b) in the presence of molecular oxygen by catalysis of the imide compound of the formula (1) to yield the carbonyl compound of the formula (17).

This process corresponds to a case in which a compound having a hydrogen atom as $R^e$ is employed as the active olefin of the formula (3) in the production of the hydroxy compound. In this case, the carbonyl compound of the formula (17) is formed instead of, or in addition to a compound corresponding to the formula (15) ($R^e$=H) and/or a compound corresponding to the formula (16) ($R^e$=H). The proportion of the formed both compounds can be controlled by appropriately selecting reaction conditions such as reaction temperature, amount of the catalyst, and the type of the co-catalyst (metallic compound).

The carbonyl compound of the formula (17) is supposed to be formed by the oxidation of the compound corresponding to the formula (15) ($R^e$=H) in a system.

Of the carbonyl compounds of the formula (17) thus prepared, preferred compounds are compounds where $R^o$, $R^p$, and $R^q$ are combined to form a bridged cyclic carbon ring (e.g., adamantane ring) with the adjacent carbon atom, each of $R^c$ and $R^d$ is a hydrogen atom or a $C_1$–$C_4$ alkyl group, Y is an alkoxycarbonyl group (e.g., a $C_1$–$C_4$ alkoxy-carbonyl group), an aryloxycarbonyl group, an acyl group (e.g., a $C_1$–$C_4$ acyl group, or a benzoyl group) or a carboxyl group. Such compounds are useful as, for example, materials for pharmaceuticals, agricultural chemicals, and other fine chemicals, and materials for functional polymers.

7. Production of Compound Having Electron Attracting Group

According to the invented process for producing a compound having an electron attracting group, the compound of the formula (14) having a methine carbon atom is allowed to react with the active olefin of the formula (3c) in the presence of molecular oxygen by catalysis of the imide compound of the formula (1) to yield the organic compound of the formula (18).

This process corresponds to a case in which a compound having hydrogen atoms as $R^c$ and $R^d$ is employed as the active olefin of the formula (3) in the production of the hydroxy compound. In this process, the compound of the formula (18) is formed instead of, or in addition to a compound corresponding to the formula (15) ($R^c$=$R^d$=H), a compound corresponding to the formula (16) ($R^c$=$R^d$=H) or a compound corresponding to the formula (17) (only in the case where $R^c$=$R^d$=H, and $R^e$=H). The proportion of the formed individual compounds can be controlled by appropriately selecting reaction conditions such as reaction temperature, amount of the catalyst, and the type of the co-catalyst (metallic compound).

The compound of the formula (18) is supposed to be formed in the following manner. The methylol group of a compound corresponding to the formula (16) ($R^c$=$R^d$=H) is further oxidized in the system to yield a carboxyl group, and the carboxyl group undergoes decarboxylation to yield the compound of the formula (0.18).

Of the carbonyl compounds of the formula (18) thus prepared, preferred compounds include compounds where $R^o$, $R^p$, and $R^q$ are combined to form a bridged cyclic carbon ring (e.g., adamantane ring) with the adjacent carbon atom, $R^e$ is a hydrogen atom or a $C_1$–$C_4$ alkyl group, and Y is an alkoxycarbonyl group (e.g., a $C_1$–$C_4$ alkoxy-carbonyl group), an aryloxycarbonyl group, an acyl group (e.g., a $C_1$–$C_4$ acyl group or a benzoyl group) or a carboxyl group. Such compounds are useful as, for example, materials for pharmaceuticals, agricultural chemicals, and other fine chemicals, and materials for functional polymers.

8. Production of Alcohol

The alcohol of the formula (19) can be produced by allowing the alcohol of the formula (2) to react with the compound of the formula (14) having a methine carbon atom in the presence of molecular oxygen by catalysis of the imide compound of the formula (1).

The alcohols of the formula (2) include similar alcohols as in the production of the 1,3-dihydroxy compound. The compounds of the formula (14) having a methine carbon atom include similar compounds as in the production of the hydroxy compound. In this process, the compound of the formula (14) having a methine carbon atom is supposed to serve as the radical scavenging compound (B2).

A reaction can be performed in accordance with the invented process for producing an organic compound. Reaction products can be separated and purified by the same separation means as above.

According to the reaction, the alcohol of the formula (19) is supposed to be formed in the following manner. A 1-hydroxyalkyl radical formed in a system and corresponding to the alcohol of the formula (2) attacks the methine carbon atom of the compound of the formula (14) to yield the alcohol of the formula (19).

9. Production of Coupling Product

The coupling product (a hydrocarbon) of the formula (20) can be obtained by allowing the compound of the formula (14a) having a methine carbon atom to react with the compound of the formula (14b) having a methine carbon atom in the presence of molecular oxygen by catalysis of the imide compound of the formula (1).

In the formulae (14a) and (14b), the organic groups and preferred organic groups in $R^{o1}$, $R^{p1}$, $R^{q1}$, $R^{o2}$, $R^{p2}$, and $R^{q2}$ include organic groups similar to those in $R^o$, $R^p$, and $R^q$. The rings formed by $R^{o1}$, $R^{p1}$, and $R^{q1}$ ($R^{o1}$ and $R^{p1}$, $R^{p1}$ and $R^{q1}$ and $R^{o1}$, or $R^{o1}$ and $R^{p1}$ and $R^{q1}$) together with the adjacent carbon atom, and the rings formed by $R^{o2}$, $R^{p2}$, and $R^{q2}$ ($R^{o2}$ and $R^{p2}$, $R^{p2}$ and $R^{q2}$, $R^{o2}$ and $R^{q2}$, or $R^{o2}$ and $R^{p2}$ and $R^{q2}$) include rings similar to those formed by $R^o$, $R^p$, and $R^q$ with the adjacent carbon atom.

The compounds of the formulae (14a) and (14b) each having a methine carbon atom include the compounds exemplified as the compounds (A3) such as the bridged cyclic compounds (A3–1a), the non-aromatic cyclic compounds (A3–1b) each having a hydrocarbon group bonded to its ring, and the chain compounds (A3–2) each having a methine carbon atom. The compound of the formula (14a) and the compound of the formula. (14b) may be identical to or different from each other.

A reaction can be performed in accordance with the invented process for producing an organic compound. Reaction products can be separated and purified by the same separation means as above.

In this reaction, the coupling product of the formula (20) is supposed to be formed in the following manner. A radical is formed at the methine carbon position of the compound of the formula (14a), and this radical attacks the methine carbon atom of the compound of the formula (14b) to yield the coupling product of the formula (20).

As thus described, the invented process can efficiently produce a variety of organic compound by an addition or substitution reaction under mild conditions. The invented process can further bond a hydroxymethyl group, an alkoxymethyl group, an acyl group, a tertiary carbon atom or the like directly to a carbon atom constituting an unsaturated bond of an unsaturated compound or a methine carbon atom of a bridged cyclic compound. In addition, the invented process can yield a corresponding 1,3-dihydroxy compound from an alcohol, an unsaturated compound, and oxygen in a good yield.

According to the invention, an α-hydroxy-γ-butyrolactone derivative can be efficiently produced under mild conditions from easily available materials.

The invention can easily and efficiently produce a hydroxy-γ-butyrolactone derivative from the α-hydroxy-γ-butyrolactone derivative.

The invention can provide novel α-hydroxy-γ-butyrolactone derivatives. These compounds are useful as materials for pharmaceuticals, agricultural chemicals, and other fine chemicals, photosensitive resins and other functional polymers.

The invented photosensitive resinous composition contains a polymer having a specific structural unit and is rapidly and surely dissolved in a developer by actin of an acid which is generated from a light-activatable acid generator through light irradiation. The composition can therefore improve developing efficiency and has satisfactory definition (resolution) and can stably and precisely form fine patterns. The composition can greatly improve the adhesion of a resist film to a substrate.

The invented polymer is useful for obtaining the photosensitive resinous composition.

The invention further provides novel α-hydroxy-γ-butyrolactone derivatives each having a bridged cyclic hydrocarbon group bonded to the γ-position, and (meth)acryloyl derivatives thereof. These compounds are useful as materials for acid-sensitive polymers, and other photosensitive resins constituting photoresist resinous compositions, and materials for fine chemicals.

The invention can produce a corresponding conjugated unsaturated compound from an alcohol, an unsaturated compound, and oxygen.

In addition, the invention can produce a corresponding β-hydroxyacetal compound from an acetal, an unsaturated compound, and oxygen in a good yield.

Furthermore, the invention can produce a corresponding hydroxy compound from a compound having a methine carbon atom, an unsaturated compound, and oxygen in a good yield.

The invention can produce a corresponding carbonyl compound from a compound having a methine carbon atom, an unsaturated compound, and oxygen in a good yield.

The invention can also produce a compound having an electron attracting group from a compound having a methine carbon atom, an unsaturated compound, and oxygen in a good yield.

Further, the invention can produce a corresponding coupling product (an alcohol) from an alcohol, a compound having a methine carbon atom, and oxygen in a good yield.

In addition and advantageously, the invention can produce a corresponding coupling product (a hydrocarbon) from a compound having a methine carbon atom, and oxygen in a good yield.

The present invention will now be illustrated in further detail with reference to several examples below, which are not intended to limit the scope of the invention.

EXAMPLE 1

A mixture of 3 mmol of ethyl acrylate, 3 ml of 2-propanol, 0.6 mmol of N-hydroxyphthalimide, 0.015 mmol of cobalt (II) acetate, and 0.045 mmol of acetylacetonatocobalt(III), and 1 ml of acetonitrile was stirred at 50° C. in an oxygen atmosphere (1 atm) for 5 hours. A gas chromatographic analysis of products in a reaction mixture revealed that ethyl 2,4-dihydroxy-4-methylpentanoate and α-hydroxy-γ,γ-dimethyl-γ-butyrolactone were formed in yields of 35% and 35%, respectively. The conversion rate from ethyl acrylate was 81%.

After 5-hour stirring at 50° C., the mixture was stirred at 70° C. for further 4 hours, and the yield of α-hydroxy-γ,γ-dimethyl-γ-butyrolactone became 71%.

EXAMPLE 2

A mixture of 3 mmol of ethyl acrylate, 1 ml of 2-propanol, 0.6 mmol of N-hydroxyphthalimide, 0.06 mmol of cobalt(II) acetate, and 1 ml of acetonitrile was stirred at 60° C. in an oxygen atmosphere (1 atm) for 5 hours. A gas chromatographic analysis of products in a reaction mixture revealed that ethyl 2,4-dihydroxy-4-methylpentanoate and α-hydroxy-γ,γ-dimethyl-γ-butyrolactone were formed in yields of 1% and 43%, respectively. The conversion rate from ethyl acrylate was 53%.

EXAMPLE 3

A mixture of 3 mmol of ethyl methacrylate, 4 ml of 2-propanol, 0.6 mmol of N-hydroxyphthalimide, 0.015 mmol of cobalt(II) acetate, and 0.045 mmol of acetylacetonatocobalt(III), and 1 ml of acetonitrile was stirred at 70° C. in an oxygen atmosphere (1 atm) for 5 hours. A gas chromatographic analysis of products in a reaction mixture revealed that ethyl 2,4-dihydroxy-2,4-dimethylpentanoate and α-hydroxy-α,γ,γ-trimethyl-γ-butyrolactone were formed in yields of 1% and 65%, respectively. The conversion rate from ethyl methacrylate was 85%.

[Spectrum Data of α-Hydroxy-α,γ,γ-trimethyl-γ-butyrolactone]

$^1$H-NMR δ: 1.46 (s, 3H), 1.53 (s, 3H), 1.54 (s, 3H), 2.10 (d, 1H, J=14 Hz), 2.32 (d, 1H, J=14 Hz), 2.91 (s, 1H)

$^{13}$C-NMR δ: 26.2, 29.0, 48.4, 74.9, 82.3, 178.6

EXAMPLE 4

A mixture of 3 mmol of adamantane, 0.6 mmol of N-hydroxyphthalimide, 0.06 mmol of acetylacetonatovanadium(III), and 1 ml of acetic acid was stirred at 90° C. in an oxygen atmosphere (1 atm) for 6 hours. A gas chromatographic analysis of products in a reaction mixture revealed that biadamantyl was formed in a yield of 2.7%.

EXAMPLE 5

A mixture of 3 mmol of ethyl acrylate, 3 ml of 2-propanol, 0.6 mmol of N-hydroxyphthalimide, 0.003 mmol of cobalt (II) acetate, 0.015 mmol of acetylacetonatocobalt(III), and 1 ml of acetonitrile was stirred at 60° C. in an oxygen atmosphere (1 atm) for 12 hours. A gas chromatographic analysis of products in a reaction mixture revealed that ethyl 2,4-dihydroxy-4-methylpentanoate and α-hydroxy-γ,γ-dimethyl-γ-butyrolactone were formed in yields of 1.5% and 75%, respectively, with a conversion from ethyl acrylate of 81%.

[Spectrum Data of α-Hydroxy-γ,γ-dimethyl-γ-butyrolactone]

$^1$H-NMR (CDCl$_3$) δ: 1.42 (s, 3H), 1.51 (s, 3H), 2.06 (dd, 1H), 2.52 (dd, 1H), 3.03 (brs, 1H), 4.63 (t, 1H)

EXAMPLE 6

A mixture of 3 mmol of ethyl acrylate, 1 ml of 2-propanol, 0.6 mmol of N-hydroxyphthalimide, 0.06 mmol of cobalt(II) acetate, and 1 ml of acetonitrile was stirred at 60° C. in an oxygen atmosphere (1 atm) for 5 hours. A gas chromatographic analysis of products in a reaction mixture revealed that ethyl 2,4-dihydroxy-4-methylpentanoate and α-hydroxy-γ,γ-dimethyl-γ-butyrolactone were formed in yields of 1% and 43%, respectively. The conversion rate from ethyl acrylate was 53%.

EXAMPLE 7

A mixture of 3 mmol of ethyl methacrylate, 4 ml of 2-propanol, 0.6 mmol of N-hydroxyphthalimide, 0.015 mmol of cobalt(II) acetate, 0.045 mmol of acetylacetonatocobalt (III), and 1 ml of acetonitrile was stirred at 70° C. in an oxygen atmosphere (1 atm) for 5 hours. A gas chromatographic analysis of products in a reaction mixture revealed that ethyl 2,4-dihydroxy-2,4-dimethylpentanoate and α-hydroxy-α,γ,γ-trimethyl-γ-butyrolactone were formed in yields of 1% and 65%, respectively. The conversion rate from ethyl methacrylate was 85%.

[Spectrum Data of α-Hydroxy-α,γ,γ-trimethyl-γ-butyrolactone]

$^1$H-NMR (CDCl$_3$) δ: 1.46 (s, 3H), 1.53 (s, 3H), 1.54 (s, 3H), 2.10 (d, 1H, J=14 Hz), 2.32 (d, 1H, J=14 Hz), 2.91 (s, 1H)

$^{13}$C-NMR (CDCl$_3$) δ: 26.2, 29.0, 48.4, 74.9, 82.3, 178.6

EXAMPLE 8

A mixture of 3 mmol of ethyl acrylate, 1.5 ml of cyclopentanol, 0.6 mmol of N-hydroxyphthalimide, 0.003 mmol of cobalt(II) acetate, 0.015 mmol of acetylacetonatocobalt (III), and 2 ml of acetonitrile was stirred at 60° C. in an oxygen atmosphere (1 atm) for 7 hours. A gas chromatographic analysis of products in a reaction mixture revealed that 3-hydroxy-2-oxo-1-oxaspiro[4.4]nonane was formed in a yield of 53%. The conversion rate from ethyl acrylate was 83%.

[Spectrum Data of 3-Hydroxy-2-oxo-1-oxaspiro[4.4]nonane]

$^1$H-NMR (CDCl$_3$) δ: 1.6–1.9 (m, 7H), 2.0–2.1 (m, 1H), 2.28 (dd, 1H, J=10.5, 12.8 Hz), 2.55 (dd, 1H, J=8.1, 12.8 Hz), 3.18 (d, 1H, J=3.3 Hz), 4.61 (ddd, 1H, J=3.3, 8.1, 10.5 Hz)

$^{13}$C-NMR (CDCl$_3$) δ: 23.2, 24.2, 38.6, 39.1, 40.8, 68.9, 92.2, 177.1

IR (neat) (cm$^{-1}$): 3417, 1768

EXAMPLE 9

In 1 ml of acetonitrile, 3 mmol of α-hydroxy-γ,γ-dimethyl-γ-butyrolactone was dissolved, and each one drop of water and a concentrated sulfuric acid were added to the resulting solution, and the mixture was stirred at 30° C. for 30 minutes. A gas chromatographic analysis of products in a reaction mixture revealed that β-hydroxy-γ,γ-dimethyl-γ-butyrolactone and 2,5-dihydro-5,5-dimethyl-2-furanone were formed in yields of 20% and 22%, respectively. The conversion rate from α-hydroxy-γ,γ-dimethyl-γ-butyrolactone was 42%.

[Spectrum Data of β-Hydroxy-γ,γ-dimethyl-γ-butyrolactone]

$^1$H-NMR (CDCl$_3$) δ: 1.39 (s), 1.45 (s), 2.49 (dd), 2.98 (dd), 2.95 (s), 4.13 (dd)

EXAMPLE 10

A mixture of 3 mmol of ethyl crotonate, 30 mmol of 2-propanol, 0.6 mmol of N-hydroxyphthalimide, 0.003 mmol of cobalt(II) acetate, 0.03 mmol of acetylacetonatocobalt(III), and 1 ml of acetonitrile was stirred at 70° C. in an oxygen atmosphere (1 atm) for 8 hours. A reaction mixture was subjected to column chromatography on a silica gel to yield α-hydroxy-β,γ,γ-trimethyl-γ-butyrolactone in a yield of 14% (trans/cis=74/26).

[Spectrum Data of α-Hydroxy-β,γ,γ-trimethyl-γ-butyrolactone]

[Trans-isomer]

$^1$H-NMR (CDCl$_3$) δ: 1.19 (d, 3H, J=7.0 Hz), 1.28 (s, 3H), 1.46 (s, 3H), 2.23 (dq, 1H, J=7.0, 11.4 Hz), 3.01 (brs, 1H), 4.15 (d, 1H, J=11.4 Hz)

$^{13}$C-NMR (CDCl$_3$) δ: 12.0, 22.5, 27.4, 47.7, 73.7, 84.8, 176.5

[Cis-isomer]

$^1$H-NMR (CDCl$_3$) δ: 1.03 (d, 3H, J=7.3 Hz), 1.40 (s, 3H), 1.44 (s, 3H), 2.23 (dq-like, 1H, J=7.3, 7.3 Hz), 2.87 (brs, 1H), 4.60 (d, 1H, J=7.3 Hz)

$^{13}$C-NMR (CDCl$_3$) δ: 8.5, 24.0, 27.7, 43.6, 70.9, 86.1, 177.1

EXAMPLE 11

A mixture of 3 mmol of diethyl maleate, 3 ml of 2-propanol, 0.6 mmol of N-hydroxyphthalimide, 0.003 mmol of cobalt(II) acetate, 0.021 mmol of acetylacetonatocobalt(III), and 1 ml of acetonitrile was stirred at 70° C. in an oxygen atmosphere (1 atm) for 6 hours. A reaction mixture was subjected to column chromatography on a silica gel to yield α-hydroxy-β-ethoxycarbonyl-γ,γ-dimethyl-γ-butyrolactone in a yield of 72% (trans/cis=76/24). The conversion rate from diethyl maleate was 90%.

[Spectrum Data of α-Hydroxy-β-ethoxycarbonyl-γ,γ-dimethyl-γ-butyrolactone]

[Trans-isomer]

$^{13}$C-NMR (CDCl$_3$) δ: 14.1, 24.0, 28.8, 58.0, 61.8, 69.8, 81.6, 168.6, 174.4

[Cis-isomer]

$^{13}$C-NMR (CDCl$_3$) δ: 14.1, 25.0, 28.2, 55.3, 61.7, 69.5, 81.8, 169.3, 174.2

EXAMPLE 12

A mixture of 3 mmol of diethyl fumarate, 3 ml of 2-propanol, 0.6 mmol of N-hydroxyphthalimide, 0.003 mmol of cobalt(II) acetate, 0.021 mmol of acetylacetonatocobalt(III), and 1 ml of acetonitrile was stirred at 60° C. in an oxygen atmosphere (1 atm) for 10 hours. A reaction mixture was subjected to column chromatography on a silica gel to yield α-hydroxy-β-ethoxycarbonyl-γ,γ-dimethyl-γ-butyrolactone in a yield of 63% (trans/cis=75/25). The conversion rate from diethyl fumarate was 97%.

EXAMPLE 13

A mixture of 3 mmol of diethyl cinnamate, 3 ml of 2-propanol, 0.6 mmol of N-hydroxyphthalimide, 0.015 mmol of cobalt(II) acetate, 0.03 mmol of acetylacetonatocobalt(III), and 1 ml of acetonitrile was stirred at 70° C. in an oxygen atmosphere (1 atm) for 12 hours. A gas chromatographic analysis of products in a reaction mixture revealed that α-hydroxy-β-phenyl-γ,γ-dimethyl-γ-butyrolactone and ethyl 2,4-dihydroxy-4-methyl-3-phenylpentanoate were formed in yields of 18% and 24%, respectively. The conversion rate from diethyl cinnamate was 61%.

[Spectrum Data of α-Hydroxy-β-phenyl-γ,γ-dimethyl-γ-butyrolactone (mixture of two isomers)]

$^1$H-NMR (CDCl$_3$) δ: 1.32, 1.41, 1.44 and 1.52 (4s, 6H), 3.00 (brs, 1H), 3.23 (m, 1H), 4.66 (m, 1H), 7.1–7.9 (m, 5H)

EXAMPLE 14

A mixture of 3 mmol of methyl acrylate, 15 mmol of 2-octanol, 0.6 mmol of N-hydroxyphthalimide, 0.003 mmol of cobalt(II) acetate, and 0.03 mmol of acetylacetonatocobalt(III), and 1 ml of acetonitrile was stirred at 50° C. in an oxygen atmosphere (1 atm) for 8 hours. A reaction mixture was subjected to column chromatography on a silica gel to yield γ-hexyl-α-hydroxy-γ-methyl-γ-butyrolactone in a yield of 74%.

[Spectrum Data of γ-Hexyl-α-hydroxy-γ-methyl-γ-butyrolactone (two isomers)]

$^1$H-NMR (CDCl$_3$) δ: 0.89 (t, 3H, J=6.8 Hz), 1.2–1.4 (m, 8H), 1.47 (s, 3H), 1.55–1.7 (m, 2H), 2.00 (dd, 1H, J=9.2, 13.2 Hz), 2.56 (dd, 1H, J=8.8, 13.2 Hz), 3.16 (brs, 1H), 4.61 (dd-like, 1H, J=9.2 Hz)

$^{13}$C-NMR (CDCl$_3$) δ: 14.0, 22.5, 24.0, 27.0, 29.4, 31.6, 40.8, 41.4, 68.8, 85.2, 177.4 IR (neat) (cm$^{-1}$): 3436, 1768 and $^1$H-NMR (CDCl$_3$) δ: 0.89 (t, 3H, J=6.8 Hz), 1.2–1.4 (m, 8H), 1.38 (s, 3H), 1.69–1.74 (m, 2H), 2.07 (dd, 1H, J=10.3, 12.6 Hz), 2.44 (dd, 1H, J=8.8, 12.6 Hz), 3.33 (brs, 1H), 4.67 (dd, 1H, J=8.8, 10.3 Hz)

$^{13}$C-NMR (CDCl$_3$) δ: 14.0, 22.5, 23.4, 25.5, 29.3, 31.6, 41.2, 41.7, 68.4, 84.6, 177.5 IR (neat) (cm$^{-1}$): 3438, 1768

EXAMPLE 15

A mixture of 3 mmol of methyl acrylate, 15 mmol of 3,3-dimethyl-2-butanol, 0.6 mmol of N-hydroxyphthalimide, 0.003 mmol of cobalt(II) acetate, 0.03 mmol of acetylacetonatocobalt(III), and 1 ml of acetonitrile was stirred at 60° C. in an oxygen atmosphere (1 atm) for 8 hours. A reaction mixture was subjected to column chromatography on a silica gel to yield γ-t-butyl-α-hydroxy-γ-methyl-γ-butyrolactone in a yield of 71%.

[Spectrum Data of γ-t-Butyl-α-hydroxy-γ-methyl-γ-butyrolactone (two isomers)]

$^1$H-NMR (CDCl$_3$) δ: 0.99 (s, 9H), 1.37 (s, 3H), 2.25 (dd, 1H, J=10.3, 12.8 Hz), 2.31 (dd, 1H, J=9.2, 12.8 Hz), 3.03 (brs, 1H), 4.68 (dd-like, 1H J=9.2, 10.3 Hz)

$^{13}$C-NMR (CDCl$_3$) δ: 22.0, 24.6, 37.1, 37.3, 68.6, 88.6, 177.5

IR (neat) (cm$^{-1}$): 3421, 1753 and $^1$H-NMR (CDCl$_3$) δ: 0.96 (s, 9H), 1.48 (s, 3H), 1.87 (dd, 1H, J=7.0, 13.9 Hz), 2.73 (dd, 1H, J=9.9, 13.9 Hz), 3.37 (brs, 1H), 4.56 (dd, 1H, J=7.0, 9.9 Hz)

$^{13}$C-NMR (CDCl$_3$) δ: 24.7, 24.9, 37.4, 38.1, 69.2, 90.8, 177.7

IR (neat) (cm$^{-1}$): 3405, 1755

EXAMPLE 16

A mixture of 3 mmol of methyl acrylate, 15 mmol of 3,3-dimethyl-2-butanol, 0.3 mmol of N-hydroxyphthalimide, 0.003 mmol of cobalt(II) acetate, 0.03 mmol of acetylacetonatocobalt(III), and 1 ml of acetonitrile was stirred at 50° C. in an oxygen atmosphere (1 atm) for 5 hours. A reaction mixture was subjected to column chromatography on a silica gel to yield 3-hydroxy-2-oxo-1-oxaspiro[4.5]decane in a yield of 83%.

[Spectrum Data of 3-Hydroxy-2-oxo-1-oxaspiro[4.5]decane]

$^1$H-NMR (CDCl$_3$) δ: 1.3–1.4 (m, 1H), 1.42–1.59 (m, 4H), 1.62–1.88 (m, 5H), 1.95 (dd, 1H, J=9.9, 12.8 Hz), 2.87 (brs, 1H), 4.61 (dd, 1H, J=8.8, 9.9 Hz)

$^{13}$C-NMR (CDCl$_3$) δ: 22.4, 22.6, 24.8, 36.7, 38.2, 41.4, 68.2, 84.3, 177.2

IR (neat) (cm$^{-1}$): 3421, 1749

EXAMPLE 17

A mixture of 3 mmol of methyl acrylate, 30 mmol of hexanol, 0.6 mmol of N-hydroxyphthalimide, 0.003 mmol of cobalt(II) acetate, 0.03 mmol of acetylacetonatocobalt (III), and 1 ml of acetonitrile was stirred at 60° C. in an oxygen atmosphere (1 atm) for 5 hours. A reaction mixture was subjected to column chromatography on a silica gel to yield α-hydroxy-γ-pentyl-γ-butyrolactone in a yield of 46% and ethyl β-hexanoyl-α-hydroxypropionate in a yield of 40%.

[Spectrum Data of α-Hydroxy-γ-pentyl-γ-butyrolactone (two isomers)]

$^1$H-NMR (CDCl$_3$) δ: 0.90 (t, 3H, J=7.0 Hz), 1.2–1.5 (m, 6H), 1.6–1.7 (m, 1H), 1.73–1.81 (m, 1H), 1.88 (ddd-like, 1H, J=10.6, 11.4, 12.5 Hz), 2.70 (ddd, 1H, J=5.1, 8.4, 12.5 Hz), 2.8–3.1 (brs, 1H), 4.38 (dddd-like, 1H, J=5.1, 7.3, 10.6, 15.8 Hz), 4.54 (dd, 1H, J=8.4, 11.4 Hz)

$^{13}$C-NMR (CDCl$_3$) δ: 13.8, 22.4, 24.6, 31.4, 35.2, 37.0, 68.6, 77.3, 177.7

IR (neat) (cm$^{-1}$): 3436, 1768 and $^1$H-NMR (CDCl$_3$) δ: 0.90 (t, 3H, J=7.0 Hz), 1.2–1.5 (m, 6H), 1.55–1.61 (m, 1H), 1.64–1.71 (m, 1H), 2.25 (ddd-like, 1H, J=4.4, 8.1, 13.2 Hz), 2.36 (ddd, 1H, J=7.7, 13.2 Hz), 3.53 (brs, 1H), 4.52 (dd-like, 1H, J=7.7, 8.1 Hz), 4.66 (dddd-like, 1H, J=4.4, 7.7, 8.1 Hz)

$^{13}$C-NMR (CDCl$_3$) δ: 13.9, 22.4, 24.9, 31.3, 35.6, 35.6, 67.5, 78.9, 177.8

IR (neat) (cm$^{-1}$): 3417, 1768

EXAMPLE 18

A mixture of 3 mmol of ethyl acrylate, 30 mmol of 2-propanol, 0.3 mmol of N-hydroxyphthalimide, 0.03 mmol of cobalt(II) acetate, and 1 ml of acetonitrile was stirred at 25° C. in an oxygen atmosphere (1 atm) for 20 hours, and was then stirred at 60° C. in an argon atmosphere for further 2 hours. A gas chromatographic analysis of products in a reaction mixture revealed that α-hydroxy-γ,γ-dimethyl-γ-butyrolactone was formed in a yield of 34%. The conversion rate from ethyl acrylate was 37%.

EXAMPLE 19

A mixture of 2 mmol of ethyl 4,4,4-trifluoro-2-butenoate, 3 ml of 2-propanol, 0.2 mmol of N-hydroxyphthalimide, 0.002 mmol of cobalt(II) acetate, 0.02 mmol of acetylacetonatocobalt(III), and 1 ml of acetonitrile was stirred at 70° C. in an oxygen atmosphere (1 atm) for 12 hours. A reaction mixture was subjected to column chromatography on a silica gel to yield β-trifluoromethyl-α-hydroxy-γ,γ-dimethyl-γ-butyrolactone and ethyl 4,4,4-trifluoro-3-hydroxy-2-(1-hydroxy-1-methylethyl)butyrate in yields of 60% and 10%, respectively. The conversion rate from ethyl 4,4,4-trifluoro-2-butenoate was 85%.

[Spectrum Data of β-Trifluoromethyl-α-hydroxy-γ,γ-dimethyl-γ-butyrolactone]

[Trans-isomer]

$^1$H-NMR (CDCl$_3$) δ: 1.48 (d, 3H, J=1.5 Hz), 1.64 (s, 3H), 3.00 (dq, 1H, J$_{HF}$=11.0 Hz), 3.29 (brs, 1H), 4.77 (d, 1H, J=11.0 Hz)

$^{13}$C-NMR (CDCl$_3$) δ: 23.8, 23.9, 29.3, 68.3, 81.3, 126.2, 173.4

IR (neat) (cm$^{-1}$): 3502, 1786

[Cis-isomer]

$^1$H-NMR (CDCl$_3$) δ: 1.58 (s, 3H), 1.65 (brs, 1H), 2.99 (dq, 1H, J$_{HH}$=7.7, J$_{HF}$=9.3 Hz), 3.00 (brs, 1H), 4.74 (d, 1H, J=7.7 Hz)

[Spectrum Data of Ethyl 4,4,4-Trifluoro-3-hydroxy-2-(1-hydroxy-1-methylethyl)butyrate (two isomers)]

$^1$H-NMR (CDCl$_3$) δ: 1.25–1.29 (t, 3H), 1.33 (s, 3H), 1.50 (s, 3H), 2.83–2.91 (m, 2H), 4.15–4.18 (m, 2H), 4.57 (brs, 1H), 4.80 (brs, 1H)

IR (neat) (cm$^{-1}$): 3164, 1732 and $^1$H-NMR (CDCl$_3$) δ: 1.29–1.33 (t, 3H), 1.39 (s, 3H), 1.40 (s, 3H), 2.72–2.73 (d, 2H), 4.21–4.30 (m, 2H), 4.45–4.48 (q, 1H), 4.89–4.91 (d, 1H)

IR (neat) (cm$^{-1}$): 3436, 1708

EXAMPLE 20

A mixture of 3 mmol of methyl 3-cyano-acrylate, 30 mmol of 2-propanol, 0.6 mmol of N-hydroxyphthalimide, 0.003 mmol of cobalt(II) acetate, 0.03 mmol of acetylacetonatocobalt(III), and 1 ml of acetonitrile was stirred at 70° C. in an oxygen atmosphere (1 atm) for 8 hours. A reaction mixture was subjected to column chromatography on a silica gel to yield β-cyano-α-hydroxy-γ,γ-dimethyl-γ-butyrolactone in a yield of 68%.

[Spectrum Data of β-Cyano-α-hydroxy-γ,γ-dimethyl-γ-butyrolactone (mixture of two isomers)]

$^1$H-NMR (CDCl$_3$) δ: 1.30, 1.41, 1.52 and 1.63 (4s, 6H), 3.10 (brs, 1H), 4.25 (m, 1H), 4.65 (m, 1H)

EXAMPLE 21

A mixture of 100 mmol of α-hydroxy-γ,γ-dimethyl-γ-butyrolactone obtained in the same manner as in Example 5, 150 mmol of acryloyl chloride, 150 mmol of triethylamine, and 300 ml of toluene was stirred at 25° C. for 4 hours. Water was added to the reaction mixture and an organic layer was concentrated, and the concentrate was subjected to column chromatography on a silica gel to yield α-acryloyloxy-γ,γ-dimethyl-γ-butyrolactone in a yield of 85%.

[Spectrum Data of α-Acryloyloxy-γ,γ-dimethyl-γ-butyrolactone]

$^1$H-NMR (CDCl$_3$) δ: 1.42 (s, 3H), 1.52 (s, 3H), 2.06 (dd, 1H), 2.52 (dd, 1H), 5.65 (dd, 1H), 5.77 (dd, 1H), 6.03 (dd, 1H), 6.32 (dd, 1H)

EXAMPLE 22

A total of 100 parts by weight of a monomer mixture and 5 parts by weight of a polymerization initiator (benzoyl peroxide) were subjected to polymerization in toluene. The monomer mixture comprised 50% by weight of α-acryloyloxy-γ,γ-dimethyl-γ-butyrolactone obtained in the same manner as in Example 21, and 50% by weight of 1-(1-methacryloyloxy-1-methylethyl)adamantane. Methanol was added to the reaction mixture to precipitate a polymer. The product was purified by repeating a procedure of dissolving the precipitate in toluene and precipitating a polymer in methanol to yield a copolymer having a weight average molecular weight of about 10000 (a molecular weight in terms of polystyrene determined by GPC).

EXAMPLE 23

A total of 100 parts by weight of a monomer mixture and 5 parts by weight of a polymerization initiator (benzoyl peroxide) were subjected to polymerization in toluene. The monomer mixture comprised 40% by weight of α-acryloyloxy-γ,γ-dimethyl-γ-butyrolactone obtained in the same manner as in Example 21, and 60% by weight of 3-(1-methacryloyloxy-1-methylethyl)-1-adamantanol. Methanol was added to the reaction mixture to precipitate a polymer. The product was purified by repeating a procedure of dissolving the precipitate in toluene and precipitating a polymer in methanol to yield a copolymer having a weight average molecular weight of about 10000 (a molecular weight in terms of polystyrene determined by GPC).

EXAMPLE 24

A total of 100 parts by weight of a monomer mixture and 5 parts by weight of a polymerization initiator (benzoyl peroxide) were subjected to polymerization in toluene. The monomer mixture comprised 50% by weight of α-acryloyloxy-γ,γ-dimethyl-γ-butyrolactone obtained in the same manner as in Example 21, and 50% by weight of 3-(methacryloyloxy)-1-adamantanol. Methanol was added to the reaction mixture to precipitate a polymer. The product was purified by repeating a procedure of dissolving the precipitate in toluene and precipitating a polymer in methanol to yield a copolymer having a weight average molecular weight of about 10000 (a molecular weight in terms of polystyrene determined by GPC).

EXAMPLE 25

A series of photoresist resinous compositions were prepared using each of the copolymers obtained according to Examples 22 to 24. Specifically, 100 parts by weight of the copolymer, 15 parts by weight of triphenylsulfonium hexafluoroantimonate, and toluene as a solvent were mixed to yield a photoresist resinous composition.

The above-prepared photoresist resinous composition was applied onto a silicon wafer by spin coating to yield a photosensitive layer 1.0 μm thick. The photosensitive layer was pre-baked on a hot plate at 60° C. for 10 seconds, and was exposed to light at an exposure dose of 100 mJ/cm$^2$ using a KrF excimer stepper, and was baked at a temperature of 100° C. for 60 seconds. The film was then subjected to developing in an alkali aqueous solution (trade name: NMD-3, available from Tokyo Ooka Kogyo Co., Ltd.) for 60 seconds, and was rinsed with pure water. Thus, each of the photoresist resinous compositions could precisely provide a target pattern.

PRODUCTION EXAMPLE 1

A mixture of 3 mmol of adamantane, 18 mmol of biacetyl, 0.015 mmol of cobalt(II) acetate, and 3 ml of acetic acid was stirred at 60° C. in an oxygen atmosphere (1 atm) for 4 hours. A gas chromatographic analysis of products in a reaction mixture revealed that adamantane was converted at a rate of 86% into 1-acetyladamantane (yield: 50%), 1,3-diacetyladamantane (yield: 23%), 1-acetyl-3-adamantanol (yield: 4%), 1-adamantanol (yield: 3%), and 2-adamantanone (yield: 3%).

[Spectrum Data of 1-Acetyladamantane]
$^1$H-NMR (CDCl$_3$) δ: 1.65–1.85 (m, 12H), 2.00–2.10 (m, 3H), 2.10 (s, 3H)

PRODUCTION EXAMPLE 2

To a mixture of 45.0 g of 1-acetyladamantane obtained according to the process of Production Example 1, 100 ml of methanol, and 20 ml of a 0.1 N sodium hydroxide aqueous solution on a water bath, 4.8 g of sodium borohydride was gradually added over 30 minutes. The mixture was stirred for further 30 minutes, was neutralized with a 1 N hydrochloric acid aqueous solution, and 200 ml of water was added to the neutralized mixture. The obtained crystal was filtrated, was washed with water, and was dried in vacuo to yield 45.0 g of α-methyl-1-adamantanemethanol.

[Spectrum Data of α-Methyl-1-adamantanemethanol]
$^1$H-NMR (CDCl$_3$) δ: 1.10 (d, 3H), 1.30–1.40 (br, 1H), 1.42–1.80 (m, 12H), 1.90–2.10 (m, 3H), 3.29 (q, 1H)

PRODUCTION EXAMPLE 3

A mixture of 3 mmol of 1-adamantanol, 18 mmol of biacetyl, 0.015 mmol of cobalt(II) acetate, and 3 ml of acetic acid was stirred at 60° C. in an oxygen atmosphere (1 atm) for 4 hours. A gas chromatographic analysis of products in a reaction mixture revealed that 1-adamantanol was converted at a rate of 82% into 1-acetyl-3-adamantanol (yield: 20%), 1,3-diacetyl-5-adamantanol (yield: 5%), 1-acetyl-4-oxo-3-adamantanol and 1-acetyl-2-oxo-5-adamantanol (total yield: 2%), 1,3-adamantanediol (yield: 6%), and 4-oxo-1-adamantanol (yield: 1%).

[Spectrum Data of 1-Acetyl-3-adamantanol]
IR (cm$^{-1}$): 3401, 2897, 2854, 1683, 1430, 1019, 605
$^{13}$C-NMR (CDCl$_3$) δ: 24.3, 29.9, 34.8, 36.8, 43.9, 45.4, 49.6, 67.9, 212.4

PRODUCTION EXAMPLE 4

To a mixture of 4.0 g of 1-acetyl-3-adamantanol obtained in the same manner as in Production Example 3, 20 ml of methanol, and 2 ml of a 0.1 N sodium hydroxide aqueous solution on a water bath, 0.6 g of sodium borohydride was gradually added. The resulting mixture was stirred at room temperature for further 30 minutes, and was neutralized with a 1 N hydrochloric acid aqueous solution. To the neutralized mixture, 50 ml of water was added, and the resulting mixture was extracted with three portions of 100 ml of ethyl acetate. An organic layer was concentrated to yield 3.6 g of 3-hydroxy-α-methyl-1-adamantanemethanol.

[Spectrum Data of 3-Hydroxy-α-methyl-1-adamantanemethanol]
MS m/e: 196 ([M$^+$]), 178, 151

PRODUCTION EXAMPLE 5

A mixture of 3 mmol of cis-decalin, 18 mmol of biacetyl, 0.3 mmol of N-hydroxyphthalimide, 0.015 mmol of cobalt (II) acetate, and 3 ml of acetic acid was stirred at 75° C. in an oxygen atmosphere (1 atm) for 8 hours. A gas chromatographic analysis of products in a reaction mixture revealed that cis-decalin was converted at a rate of 67% into 4a-acetyl-cis-decalin (yield: 24%), 4a-hydroxy-cis-decalin (yield: 4%), 4a,8a-dihydroxy-cis-decalin (yield: 22%), 1,6-cyclodecanedione (yield: 10%), and 4a-acetyl-8a-hydroxy-cis-decalin (yield: 5%).

[Spectrum Data of 4a-Acetyl-cis-decalin]
MS m/e: 180 ([M$^+$]), 165, 137
[Spectrum Data of 4a-Acetyl-8a-hydroxy-cis-decalin]
MS m/e: 196 ([M$^+$]), 178, 163, 136

PRODUCTION EXAMPLE 6

The reduction procedure of Production Example 4 was repeated, except that 4a-acetyl-cis-decalin obtained in the same manner as in Production Example 5 was used to yield α-methyl-4a-decalinmethanol [4a-(1-hydroxyethyl)-cis-decalin] in a yield of 87%.

[Spectrum Data of α-Methyl-4a-decalinmethanol]
MS m/e: 182 ([M$^+$]), 164, 137

PRODUCTION EXAMPLE 7

The reduction procedure of Production Example 4 was repeated, except that 4a-acetyl-8a-hydroxy-cis-decalin obtained in the same manner as in Production Example 5 was used to yield 8a-hydroxy-α-methyl-4a-decalinmethanol [4a-hydroxy-8a-(1-hydroxyethyl)-cis-decalin] in a yield of 82%.

[Spectrum Data of 8a-Hydroxy-α-methyl-4a-decalinmethanol]
MS m/e: 198 ([M$^+$]), 180, 162, 135

PRODUCTION EXAMPLE 8

A mixture of 3 mmol of endotricyclo[5.2.1.0$^{2,6}$]decane, 18 mmol of biacetyl, 0.3 mmol of N-hydroxyphthalimide, 0.015 mmol of cobalt(II) acetate, and 3 ml of acetic acid was stirred at 75° C. in an oxygen atmosphere (1 atm) for 6 hours. A gas chromatographic analysis of products in a reaction mixture revealed that endotricyclo[5.2.1.0$^{2,6}$]decane was converted at a rate of 75% into 2-acetylendotricyclo[5.2.1.0$^{2,6}$]decane (yield: 27%), 2-hydroxyendotricyclo[5.2.1.0$^{2,6}$]decane (yield: 11%), 2,6-dihydroxyendotricyclo[5.2.1.0$^{2,6}$]decane (yield: 16%), 2-acetyl-6-hydroxyendotricyclo[5.2.1.0$^{2,6}$]decane (yield: 6%), and dicyclo[5.2.1]decane-2,6-dione (yield: 12%).

[Spectrum Data of 2-Acetylendotricyclo[5.2.1.0$^{2,6}$]decane]

MS m/e: 178 ([M$^+$]), 163, 135

[Spectrum Data of 2-Acetyl-6-hydroxyendotricyclo[5.2.1.0$^{2,6}$]decane]

MS m/e: 194 ([M$^+$]), 176, 161, 134

PRODUCTION EXAMPLE 9

The reduction procedure of Production Example 4 was repeated, except that 2-acetylendotricyclo[5.2.1.0$^{2,6}$]decane obtained in the same manner as in Production Example 8 was used to yield α-methyl-2-tricyclo[5.2.1.0$^{2,6}$]decanemethanol [2-(1-hydroxyethyl)endotricyclo[5.2.1.0$^{2,6}$]decane] in a yield of 92%.

[Spectrum Data of α-Methyl-2-tricyclo[5.2.1.0$^{2,6}$]decanemethanol]

MS m/e: 180 ([M$^+$]), 162, 135

PRODUCTION EXAMPLE 10

The reduction procedure of Production Example 4 was repeated, except that 2-acetyl-6-hydroxyendotricyclo[5.2.1.0$^{2,6}$]decane obtained in the same manner as in Production Example 8 was used to yield 6-hydroxy-α-methyl-2-tricyclo[5.2.1.0$^{2,6}$]decanemethanol [2-hydroxy-6-(1-hydroxyethyl)endotricyclo[5.2.1.0$^{2,6}$]decane] in a yield of 86%.

[Spectrum Data of 6-Hydroxy-α-methyl-2-tricyclo[5.2.1.0$^{2,6}$]decanemethanol]

MS m/e: 196 ([M$^+$]), 178, 160, 133

EXAMPLE 26

A mixture of 110 mmol of ethyl acrylate, 100 mmol of 3-hydroxy-α-methyl-1-adamantanemethanol, 10 mmol of N-hydroxyphthalimide, 0.06 mmol of acetylacetonatocobalt (II), 0.04 mmol of cobalt(III) acetate, and 200 ml of acetic acid was stirred at 60° C. in an oxygen atmosphere (1 atm) for 4 hours. A reaction mixture was subjected to column chromatography on a silica gel to yield γ-(3-hydroxyadamant-1-yl)-α-hydroxy-γ-methyl-γ-butyrolactone of the following formula in a yield of 75%. The conversion rate from 3-hydroxy-α-methyl-1-adamantanemethanol was 81%.

MS m/e: 266, 248, 230, 186, 151

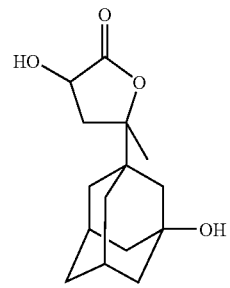

EXAMPLE 27

The procedure of Example 26 was repeated, except that 100 mmol of α-methyl-1-adamantanemethanol was used instead of 3-hydroxy-α-methyl-1-adamantanemethanol to yield γ-(1-adamantyl)-α-hydroxy-γ-methyl-γ-butyrolactone of the following formula in a yield of 88%. The conversion rate from α-methyl-1-adamantanemethanol was 95%.

MS m/e: 250, 232, 217, 173, 135

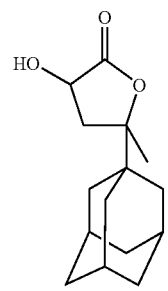

EXAMPLE 28

The procedure of Example 26 was repeated, except that 100 mmol of α-methyl-4a-decalinmethanol was used instead of 3-hydroxy-α-methyl-1-adamantanemethanol to yield γ-(4a-decalinyl)-α-hydroxy-γ-methyl-γ-butyrolactone of the following formula in a yield of 69%. The conversion rate from α-methyl-4a-decalinmethanol was 75%.

MS m/e: 252, 234, 219, 175, 136

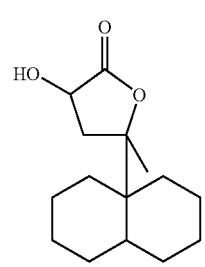

EXAMPLE 29

The procedure of Example 26 was repeated, except that 100 mmol of 8a-hydroxy-α-methyl-4a-decalinmethanol was used instead of 3-hydroxy-α-methyl-1-adamantanemethanol to yield γ-(8a-hydroxydecalin-4a-yl)-α-hydroxy-γ-methyl-γ-butyrolactone of the following formula in a yield of 67%. The conversion rate from 8a-hydroxy-α-methyl-4a-decalin-methanol was 72%.

MS m/e: 268, 250, 232, 217, 173, 134

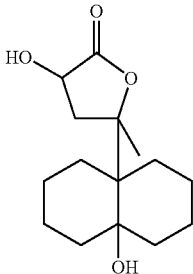

EXAMPLE 30

The procedure of Example 26 was repeated, except that 100 mmol of α-methyl-2-tricyclo[5.2.1.0$^{2,6}$]decanemethanol was used instead of 3-hydroxy-α-methyl-1-adamantanemethanol, to yield α-hydroxy-γ-methyl-γ-(2-tricyclo[5.2.1.0$^{2,6}$]decanyl)-γ-butyrolactone of the following formula in a yield of 80%. The conversion rate from α-methyl-2-tricyclo[5.2.1.0$^{2,6}$]decanemethanol was 84%.

MS m/e: 250, 232, 217, 173, 134

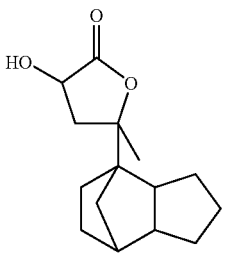

EXAMPLE 31

The procedure of Example 26 was repeated, except that 100 mmol of 6-hydroxy-α-methyl-2-tricyclo[5.2.1.0$^{2,6}$]decanemethanol was used instead of 3-hydroxy-α-methyl-1-adamantanemethanol, to yield α-hydroxy-γ-(6-hydroxytricyclo[5.2.1.0$^{2,6}$]decan-2-yl)-γ-methyl-γ-butyrolactone of the following formula in a yield of 73%. The conversion rate from 6-hydroxy-α-methyl-2-tricyclo[5.2.1.0$^{2,6}$]decanemethanol was 80%.

MS m/e: 266, 248, 230, 215, 171, 132

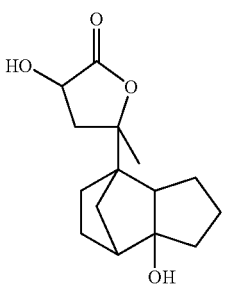

EXAMPLE 32

A mixture of 100 mmol of γ-(1-adamantyl)-α-hydroxy-γ-methyl-γ-butyrolactone obtained in the same manner as in Example 27, 150 mmol of acryloyl chloride, 150 mmol of triethylamine, and 300 ml of toluene was stirred at 60° C. for 6 hours. A reaction mixture was subjected to column chromatography on a silica gel to yield α-acryloyloxy-γ-(1-adamantyl)-γ-methyl-γ-butyrolactone of the following formula in a yield of 66%. The conversion rate from γ-(1-adamantyl)-α-hydroxy-γ-methyl-γ-butyrolactone was 85%.

MS m/e: 304, 232, 217, 173, 135

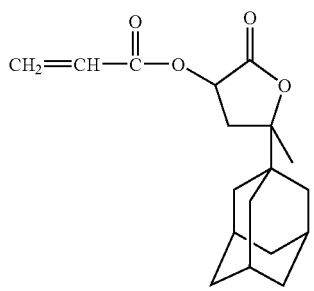

EXAMPLE 33

A mixture of 10 mmol of ethyl acrylate, 100 mmol of n-propyl alcohol, 1 mmol of N-hydroxyphthalimide, 0.01 mmol of cobalt(II) acetate, 0.1 mmol of acetylacetonatocobalt(III), and 54 mmol of acetonitrile was stirred at 50° C. in an oxygen atmosphere (1 atm) for 8 hours. A reaction mixture was concentrated, and the concentrate was subjected to column chromatography on a silica gel to yield ethyl 2,4-dihydroxyhexanoate, γ-ethyl-α-hydroxy-γ-butyrolactone, and ethyl sorbate in yields of 14%, 40%, and 2%, respectively. The conversion rate from ethyl acrylate was 72%.

[Spectrum Data of Ethyl 2,4-Dihydroxyhexanoate]

MS (EI) m/e: 176, 148, 140, 85

[Spectrum Data of γ-Ethyl-α-hydroxy-γ-butyrolactone]

MS (EI) m/e: 102, 83, 59, 44

[Spectrum Data of Ethyl Sorbate]

MS (EI) m/e: 140, 125, 112, 95, 67

EXAMPLE 34

A mixture of 10 mmol of ethyl acrylate, 100 mmol of 2-methyl-1,3-dioxolane, 1 mmol of N-hydroxyphthalimide, 0.01 mmol of cobalt(II) acetate, 0.1 mmol of acetylacetonatocobalt(III), and 54 mmol of acetonitrile was stirred at 50° C. in an oxygen atmosphere (1 atm) for 8 hours. A reaction mixture was concentrated, and the concentrate was subjected to column chromatography on a silica gel to yield a β-hydroxyacetal compound of the following formula in a yield of 90%. The conversion rate from ethyl acrylate was 99%.

MS (EI) m/e: 204, 186, 159, 46

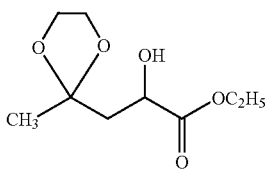

EXAMPLE 35

A mixture of 10 mmol of ethyl acrylate, 100 mmol of 1,3-dioxolane, 1 mmol of N-hydroxyphthalimide, 0.01 mmol of cobalt(II) acetate, 0.1 mmol of acetylacetonatocobalt(III), and 54 mmol of acetonitrile was stirred at 50° C. in an oxygen atmosphere (1 atm) for 8 hours. A reaction mixture was concentrated, and the concentrate was subjected to column chromatography on a silica gel to yield a β-hydroxyacetal compound of the following formula in a yield of 99%. The conversion rate from ethyl acrylate was 99%.

MS (EI) m/e: 190, 172, 145, 46

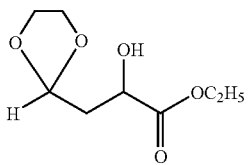

EXAMPLE 36

A mixture of 10 mmol of ethyl acrylate, 50 mmol of adamantane, 1 mmol of N-hydroxyphthalimide, 0.01 mmol of cobalt(II) acetate, 0.1 mmol of acetylacetonatocobalt(III), and 54 mmol of acetonitrile was stirred at 70° C. in an oxygen atmosphere (1 atm) for 8 hours. A reaction mixture was concentrated, and the concentrate was subjected to column chromatography on a silica gel to yield ethyl 3-(adamant-1-yl)-2-hydroxypropionate of the following formula (a), ethyl 3-(adamant-1-yl)-2-oxopropionate of the following formula (b), and ethyl 1-adamantaneacetate of the following formula (c) in yields of 55%, 16%, and 8%, respectively. The conversion rate from ethyl acrylate was 99%.

[Spectrum Data of Ethyl 3-(Adamant-1-yl)-2-hydroxypropionate]

MS (EI) m/e: 252, 234, 135, 46

[Spectrum Data of Ethyl 3-(Adamant-1-yl)-2-oxopropionate]

MS (EI) m/e: 250, 221, 179, 135, 46

[Spectrum Data of Ethyl 1-Adamantaneacetate]

MS (EI) m/e: 222, 135, 46

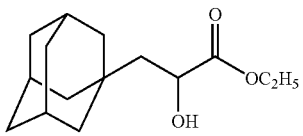

(a)

-continued

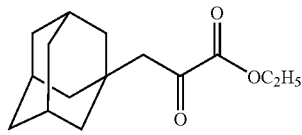

(b)

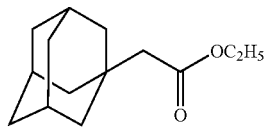

(c)

EXAMPLE 37

The procedure of Example 36 was repeated, except that 0.1 mmol of acetylacetonatovanadium(III) was used instead of 0.1 mmol of acetylacetonatocobalt(III). As a result, ethyl 3-(adamant-1-yl)-2-hydroxypropionate of the formula (a), ethyl 3-(adamant-1-yl)-2-oxopropionate of the formula (b), and ethyl 1-adamantaneacetate of the formula (c) were formed in yields of 30%, 50%, and 11%, respectively. The conversion rate from ethyl acrylate was 99%.

EXAMPLE 38

A mixture of 50 mmol of 2-propanol, 10 mmol of adamantane, 1 mmol of N-hydroxyphthalimide, 0.01 mmol of cobalt(II) acetate, 0.1 mmol of acetylacetonatocobalt(III), and 54 mmol of acetonitrile was stirred at 70° C. in an oxygen atmosphere (1 atm) for 8 hours. A reaction mixture was concentrated, and the concentrate was subjected to column chromatography on a silica gel to yield α,α-dimethyl-1-damantanemethanol in a yield of 50%. The conversion rate from adamantane was 70%.

[Spectrum Data of α,α-Dimethyl-1-adamantanemethanol]

MS (EI) m/e: 179, 176, 135, 57.

The invention claimed is:

1. A process for producing an organic compound which is an addition or substitution reaction product of a compound (A) and a compound (B) or an oxidized product thereof, wherein said product is selected from the group consisting of
   (i-1) an addition reaction product or an oxidized product thereof, where an adjacent position to an oxygen atom of a compound (A1) is bonded to a carbon atom of an unsaturated bond of an unsaturated compound (B1) when an oxygen-atom-containing compound (A1) is employed as a compound (A),
   (i-2) a substitution reaction product or an oxidized product thereof, where an adjacent position to an oxygen atom of a compound (A1) is bonded to a methine carbon atom of a compound (B2) having a hydrocarbon group with a methine carbon atom when an oxygen-atom-containing compound (A1) is employed as a compound (A),
   (ii-1) an addition reaction product or an oxidized product thereof, where a bond between a carbonyl group and an atom adjacent to a carbonyl group of a compound (A2) is broken, and a group containing the a carbonyl group is bonded to the aforementioned position of a compound (B1) when a carbonyl-group-containing compound (A2) is employed as a compound (A),
   (ii-2) a substitution reaction product or an oxidized product thereof, where a bond between a carbonyl group and an atom adjacent to a carbonyl group of a compound (A2) is broken, and a group containing the a carbonyl group is bonded to the aforementioned position of a compound (B2) when a carbonyl-group-containing compound (A2) is employed as a compound (A), (iii-1) an addition reaction product or an oxidized product thereof, where a methine carbon atom of a compound (A3) is bonded to the aforementioned position of a compound (B1) when a compound (A3) containing a hydrocarbon group with a methine carbon atom is employed as a compound A, and (iii-2) a substitution reaction product or an oxidized product thereof, where a methine carbon atom of a compound (A3) is bonded to the aforementioned position of a compound (B2) when a compound (A3) containing a hydrocarbon group with a methine carbon atom is employed as a compound A, said process comprising the step of allowing (A) a compound capable of forming a stable radical and being selected from (A1) oxygen-atom-containing compounds each having a carbon-hydrogen bond at the adjacent position to an oxygen atom, (A2) carbonyl-group-containing compounds, and (A3) compounds each having a hydrocarbon group with a methine carbon atom to react with (B) a radical scavenging compound selected from (B1) unsaturated compounds, and (B2) compounds each having a hydrocarbon group with a methine carbon atom, provided that if a 1,2-dicarbonyl compound or its hydroxy reductant is used as the compound (A), the compound (B) is a radical scavenging compound (B1), in the presence of a catalytic imide compound and in the presence of molecular oxygen, by catalysis of the imide compound, wherein the imide compound is shown by the following formula (1):

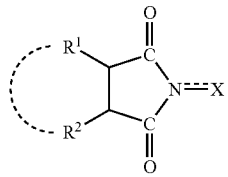

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (1) may be further bonded to said $R^1$, $R^2$, or to the double bond or aromatic or non-aromatic ring formed together by $R^1$ and $R^2$, to yield a product of an addition or substitution reaction of said compound (A) and said compound (B) or an oxidized product thereof.

2. The process for producing an organic compound according to claim 1, which process comprises an addition reaction wherein compound (A) is (A11) an alcohol shown by the following formula (2):

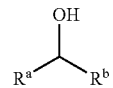

(2)

wherein each of $R^a$ and $R^b$ is, identical to or different from each other, a hydrogen atom or an organic group, where $R^a$ and $R^b$ may be combined to form a ring with the adjacent carbon atom, and compound (B) is (B12) an α,β-unsaturated carboxylic acid derivative shown by the following formula (5):

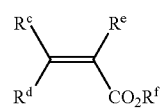

(5)

wherein each of $R_c$, $R^d$, $R^e$, and $R^f$ is, identical to or different from one another, a hydrogen atom or an organic group, where $R^c$, $R^d$, and $R^e$ may be combined to form a ring with the adjacent carbon atom or carbon—carbon bond, and wherein the organic compound which is an addition or substitution reaction product or an oxidized product thereof is an α-hydroxy-γ-butyrolactone derivative shown by the following formula (6):

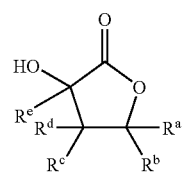

(6)

wherein $R^a$, $R^b$, $R^c$, $R^d$, and $R^e$ have the same meanings as defined above.

3. A process according to one of claims 1 or 2 and wherein a metallic compound is used as a co-catalyst.

4. A process according to claim 2 for preparing α-hydroxy-γ,γ-dimethyl-γ-butyrolactone, in which:

reactant (A) is (A1), an oxygen-atom-containing compound having a carbon-hydrogen bond at the adjacent position to an oxygen atom, and embodiment (A11) of (A1) is an alcohol of Formula (2), reactant (A) being 2-propanol;

reactant (B) is (B1), an unsaturated compound, and embodiment (B12) of (B1) is an α,β-unsaturated carboxylic acid derivative of Formula (5), reactant (B) being ethyl acrylate; and the imide compound of Formula (1) is N-hydroxyphthalimide.

5. A process for preparing α-hydroxy-γ,γ-dimethyl-γ-butyrolactone according to claim 4, wherein a metallic compound is used as a co-catalyst.

* * * * *